US012655112B2

(12) United States Patent
Nakayama et al.

(10) Patent No.: US 12,655,112 B2
(45) Date of Patent: Jun. 16, 2026

(54) CARBOXYLIC ACID OR CARBOXYLIC ACID ESTER COMPOUND HAVING FUSED-RING STRUCTURE, METHOD FOR PRODUCING THE SAME, AND USE OF COMPOUND

(71) Applicant: FUJIFILM Corporation, Tokyo (JP)

(72) Inventors: Takafumi Nakayama, Ashigarakami-gun (JP); Kosuke Chiba, Ashigarakami-gun (JP); Naoyuki Morooka, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 556 days.

(21) Appl. No.: 18/166,235

(22) Filed: Feb. 8, 2023

(65) Prior Publication Data

US 2023/0265058 A1 Aug. 24, 2023

Related U.S. Application Data

(63) Continuation of application No. PCT/JP2021/029983, filed on Aug. 17, 2021.

(30) Foreign Application Priority Data

Aug. 21, 2020 (JP) ................................ 2020-140313

(51) Int. Cl.

| | |
|---|---|
| ***C07D 241/42*** | (2006.01) |
| ***C07C 57/50*** | (2006.01) |
| ***C07C 59/72*** | (2006.01) |
| ***G02B 1/04*** | (2006.01) |

(52) U.S. Cl.

CPC ............ *C07D 241/42* (2013.01); *C07C 57/50* (2013.01); *C07C 59/72* (2013.01); *G02B 1/041* (2013.01); *C07C 2603/10* (2017.05)

(58) Field of Classification Search

CPC ....... C07D 241/42; C07C 57/50; C07C 59/72; C07C 2603/10; G02B 1/041

See application file for complete search history.

(56) References Cited

U.S. PATENT DOCUMENTS

| | | | | |
|---|---|---|---|---|
| 9,334,352 B2 * | 5/2016 | Someya | ............... | C09D 125/16 |
| 2018/0305486 A1 | 10/2018 | Nakayama et al. | | |

FOREIGN PATENT DOCUMENTS

| | | |
|---|---|---|
| JP | 2014-208804 A | 11/2014 |
| JP | 2020-105101 A | 7/2020 |
| WO | 2017/115649 A1 | 7/2017 |
| WO | 2019035461 * | 2/2019 |
| WO | 2020171039 * | 8/2020 |

OTHER PUBLICATIONS

Amin, J Org Chem, 1984, 49, 1091-1095. (Year: 1984).*

Sikkandarkani Akbar et al. “Iron-Catalyzed Tandem Conia-Ene/Friedel-Crafts Reactions of o-Alkynyldihydrochalcones: Access to Benzo[b]fluorenes”, J. Org. Chem., 2016, vol. 81, pp. 1229-1236 (8 pages total).

Chang Ho Oh et al., “Scandium-Catalyzed Intramolecular Friedel-Crafts Reactions of 2-[(2-Alkyl-1H-indol-3-yl)methylene] malonates”, Synlett, 2014, vol. 25, pp. 579-585 (9 pages total).

Zhaomeng Han et al., “Direct Assembly of 3,4-Difunctionalized Benzofurans and Polycyclic Benzofurans by Phenol Dearomatization and Palladium-Catalyzed Domino Reaction”, Angew. Chem. Int. Ed., 2014, vol. 53, pp. 6805-6809 (5 pages total).

Elizabeth Chosson et al., “First and mild synthesis of fluorene-9-malonic acid and some substituted derivatives via the intramolecular hydroarylation of 2-phenylbenzylidenemalonic acids”, Tetrahedron, 2011, vol. 67, pp. 2548-2554 (7 pages total).

Roger F. C. Brown et al., “Pyrolysis of Quinoline-3,4-dicarboxylic Anhydrides Bearing 2-Phenyl, 2-Benzyl and 2-o-Tolyl Substituents: Formation of Products of Carbene Insertion and Addition”, Tetrahedron, 1992, vol. 48, No. 36, pp. 7763-7774 (12 pages total).

Adolf Sieglitz et al., 3-Hydroxyfluoranthene-1-, -2-, and -10-carboxylic acids, Chemische Berichte, 1962, vol. 95, pp. 3013-3029 (19 pages total).

Berma L. Mcdowell et al., “1,2-Dihydrocyclopent[jk]fluorene”, Journal of the American Chemical Society, Sep. 20, 1962, vol. 84, pp. 3531-3538 (8 pages total).

T. Lloyd Fletcher et al., “Derivatives of Fluorene. Part XII. 2-Amino-9-bromo-fluorene Hydrobromide and Related Compounds.”, Journal of Chemical Society., 1961 pp. 1400-1403 (4 pages total).

(Continued)

*Primary Examiner* — D Margaret M Seaman

(74) *Attorney, Agent, or Firm* — Sughrue Mion, PLLC

(57) ABSTRACT

Provided are a compound represented by the following General Formula (A1-1), a method for producing the same, and the use of the compound:

General Formula (A1-1)

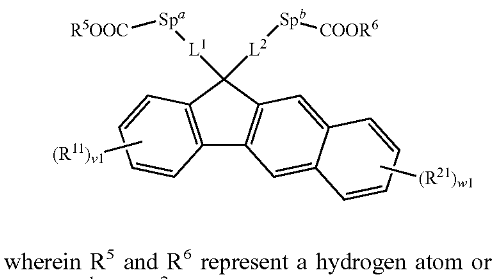

wherein $R^5$ and $R^6$ represent a hydrogen atom or an alkyl group, $L^1$ and $L^2$ represent an alkylene group having 1 to 6 carbon atoms, $Sp^a$ and $Sp^b$ represent a single bond or a divalent linking group, $R^{11}$ and $R^{21}$ represent a substituent, and v1 and w1 are an integer of 0 to 4. Further provided that a structure represented by $(R^{11})_{v1}$-benzen ring/cyclopentadiene skeleton/naphthalene ring-$(R^{21})_{w1}$ is not line-symmetrical, where “/” represents that two rings described on left and right sides of the structure are fused.

4 Claims, No Drawings

(56) References Cited

OTHER PUBLICATIONS

International Search Report issued Nov. 2, 2021 in International Application No. PCT/JP2021/029983.
Written Opinion issued Nov. 2, 2021 in International Application No. PCT/JP2021/029983.
International Preliminary Report on Patentability dated Jun. 29, 2022 issued in International Application No. PCT/JP2021/029983.

* cited by examiner

CARBOXYLIC ACID OR CARBOXYLIC ACID ESTER COMPOUND HAVING FUSED-RING STRUCTURE, METHOD FOR PRODUCING THE SAME, AND USE OF COMPOUND

CROSS-REFERENCE TO RELATED APPLICATIONS

This application is a Continuation of PCT International Application No. PCT/JP2021/029983 filed on Aug. 17, 2021, which claims priority under 35 U.S.C. § 119 (a) to Japanese Patent Application No. 2020-140313 filed in Japan on Aug. 21, 2020. Each of the above applications is hereby expressly incorporated by reference, in its entirety, into the present application.

BACKGROUND OF THE INVENTION

1. Field of the Invention

The present invention relates to a carboxylic acid or carboxylic acid ester compound having a fused-ring structure, a method for producing the same. The present invention also relates to the use of the carboxylic acid or carboxylic acid ester compound having a fused-ring structure.

2. Description of the Related Art

In the related art, glass materials have been used for an optical member of an imaging module such as a camera, a video camera, a mobile phone with a camera, a video phone, or a door phone with a camera. The glass material has optical characteristics suitable for the optical member of the imaging module, can impart desired optical characteristics, and has excellent environmental resistance.

However, it is not easy to reduce a weight and size of the glass material, and workability and productivity are also deteriorated. On the other hand, since a resin cured product can be mass-produced and has excellent workability, with the miniaturization of the imaging module in the related art, the resin cured product has been used as an optical member to replace the glass material.

With the miniaturization of the imaging module, the optical member thereof is also required to be miniaturized. However, as the optical member is smaller, the problem of chromatic aberration arises. Accordingly, in an optical member formed of the resin cured product, examinations have been conducted regarding adjusting a small Abbe number using a monomer of a curable composition and additives, thereby correcting chromatic aberrations.

For example, JP2014-208804A discloses a curable resin composition containing a fused ring-containing compound (monomer) in which a (meth)acryloyl group is bonded through a phenylene group to a fluorene-type skeleton having four or more fused rings, and discloses that a cured product exhibiting a low Abbe number (νD) is obtained by using this resin compound.

In addition, WO2017/115649A discloses a compound (monomer) in which a (meth)acryloyl group is bonded through a phenylene group to a fluorene-type skeleton including a nitrogen atom as a ring-constituting atom, and discloses that a cured product having a low Abbe number (νD) and a high partial dispersion ratio (θg, F value) is obtained by using a curable composition containing this compound.

SUMMARY OF THE INVENTION

In a resin cured product used as the optical member, purity of a raw material compound may affect light transmittance of the raw material compound or the resin cured product. Therefore, it is desired to use a high-purity raw material compound for preparing the resin cured product as an optical member. In order to obtain such a desired high-purity raw material compound, a certain degree of complication, such as that a purification step is required after synthesizing an intermediate of the raw material compound or after synthesizing the raw material compound from the intermediate, is unavoidable in the preparation of the raw material compound having a target purity.

An object of the present invention is to provide a compound suitable as a raw material compound for an optical member such as a lens or a synthetic intermediate thereof and a method for producing the same.

The above-described objects of the present invention are achieved by the following methods.

<1>

A compound represented by General Formula (A) or (B),

General Formula (A)

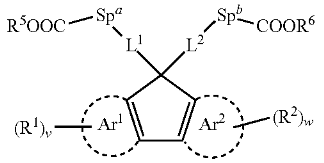

General Formula (B)

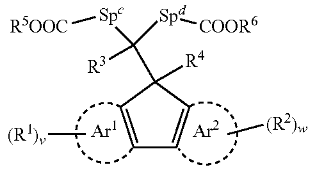

in the formulae, $R^3$ and $R^4$ represent a hydrogen atom or a monovalent substituent, $R^5$ and $R^6$ represent a hydrogen atom or an alkyl group, $L^1$ and $L^2$ represent an alkylene group having 1 to 6 carbon atoms, and $Sp^a$ to $Sp^d$ represent a single bond or a divalent linking group, a ring $Ar^1$ represents an aromatic ring represented by Formula (AR1) or a fused ring including the aromatic ring as a ring constituting the fused ring, and a ring $Ar^2$ represents an aromatic ring represented by Formula (AR2) or a fused ring including the aromatic ring as a ring constituting the fused ring, $R^1$ represents a substituent adopted by a ring-constituting atom of the ring $Ar^1$, and $R^2$ represents a substituent adopted by a ring-constituting atom of the ring $Ar^2$, v is an integer of 0 or more, and a maximum number of v is a maximum number of substituents which are able to be adopted by the ring-constituting atom of the ring $Ar^1$, and w is an integer of 0 or more, and a maximum number of w is a maximum number of substituents which are able to be adopted by the ring-constituting atom of the ring $Ar^2$, Formula (AR1)

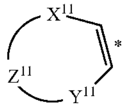

Formula (AR2)

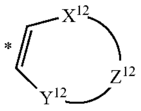

in the formulae, $X^{11}$, $Y^{11}$, $X^{12}$, and $Y^{12}$ represent an oxygen atom, a sulfur atom, a nitrogen atom, or a carbon atom, $Z^{11}$ represents an atomic group which forms a 5- to 7-membered aromatic ring together with $—X^{11}—C{=}C—Y^{11}—$ and is composed of atoms selected from an oxygen atom, a sulfur atom, a nitrogen atom, and a carbon atom.

$Z^{12}$ represents an atomic group which forms a 5- to 7-membered aromatic ring together with $—X^{12}—C{=}C—Y^{12}—$ and is composed of atoms selected from an oxygen atom, a sulfur atom, a nitrogen atom, and a carbon atom, and

* corresponds to a double bond of a cyclopentadiene ring in General Formula (A) or (B), provided that in General Formulae (A) and (B), a structure represented by $(R^1)_v—Ar^1$/cyclopentadiene skeleton/$Ar^2—(R^2)_w$ is not line-symmetrical, in which "/" represents that the two rings described on left and right sides of the structure are fused, and it is not allowed that one of the ring $Ar^1$ or the ring $Ar^2$ is a benzene ring and the other is a quinoline ring.

<2>

The compound according to <1>, in which the compound is represented by General Formula (A).

<3>

The compound according to <2>, in which the compound is represented by General Formula (A1), General Formula (A1)

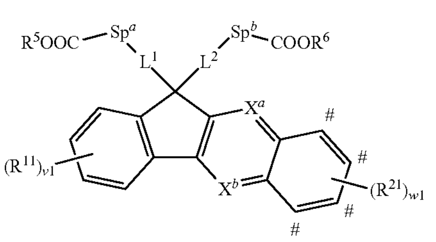

in the formula, $X^a$ and $X^b$ represent a nitrogen atom or CH, CH at a position of # may be substituted by a nitrogen atom, $R^{11}$ and $R^{21}$ represent a substituent and v1 and w1 are an integer of 0 to 4, and $L^1$, $L^2$, $Sp^a$, $Sp^b$, $R^5$, and $R^6$ have the same meanings as $L^1$, $L^2$, $Sp^a$, $Sp^b$, $R^5$, and $R^6$ in General Formula (A), respectively, provided that in a case where one of $X^a$ or $X^b$ is a nitrogen atom, at least one of CH's at the position of # is a nitrogen atom, and in a case where both $X^a$ and $X^b$ are CH, it is not allowed that only one of CH at the position of #, which is bonded to the same carbon atom as $X^a$, or CH at the position of #, which is bonded to the same carbon atom as $X^b$, is substituted by a nitrogen atom.

<4>

A method for producing a compound represented by General Formula (A), the method comprising:

obtaining a compound represented by General Formula (A) by subjecting (i) an ethylenically unsaturated carboxylic acid compound, (ii) an ethylenically unsaturated carboxylic acid ester compound, (iii) an ethylenically unsaturated dicarboxylic acid anhydride, or (iv) an alkylcarboxylic acid ester compound having a leaving group at a ω-position to an addition reaction with a compound represented by General Formula (S) in the presence of a base, General Formula (S)

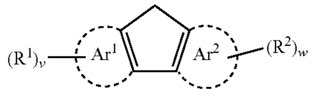

General Formula (A)

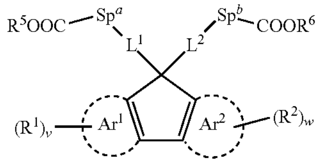

in the formulae, $R^5$ and $R^6$ represent a hydrogen atom or an alkyl group, $L^1$ and $L^2$ represent an alkylene group having 1 to 6 carbon atoms, and $Sp^a$ and $Sp^b$ represent a single bond or a divalent linking group, a ring $Ar^1$ represents an aromatic ring represented by Formula (AR1) or a fused ring including the aromatic ring as a ring constituting the fused ring, and a ring $Ar^2$ represents an aromatic ring represented by Formula (AR2) or a fused ring including the aromatic ring as a ring constituting the fused ring, $R^1$ represents a substituent adopted by a ring-constituting atom of the ring $Ar^1$, and $R^2$ represents a substituent adopted by a ring-constituting atom of the ring $Ar^2$, v is an integer of 0 or more, and a maximum number of v is a maximum number of substituents which are able to be adopted by the ring-constituting atom of the ring $Ar^1$, and w is an integer of 0 or more, and the maximum number of w is the maximum number of substituents which are able to be adopted by the ring-constituting atom of the ring $Ar^2$, Formula (AR1)

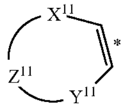

Formula (AR2)

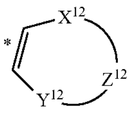

in the formulae, $X^{11}$, $Y^{11}$, $X^{12}$, and $Y^{12}$ represent an oxygen atom, a sulfur atom, a nitrogen atom, or a carbon atom, $Z^{11}$ represents an atomic group which forms a 5- to 7-membered aromatic ring together with $—X^{11}—C═C—Y^{11}—$ and is composed of atoms selected from an oxygen atom, a sulfur atom, a nitrogen atom, and a carbon atom, $Z^{12}$ represents an atomic group which forms a 5- to 7-membered aromatic ring together with $—X^{12}—C═C—Y^{12}—$ and is composed of atoms selected from an oxygen atom, a sulfur atom, a nitrogen atom, and a carbon atom, and

* corresponds to a double bond of a cyclopentadiene ring in General Formulae (S) and (A), provided that in General Formulae (S) and (A), a structure represented by $(R^1)_v—Ar^1$/cyclopentadiene skeleton/$Ar^2—(R^2)_w$ is not line-symmetrical, in which "/" represents that the two rings described on left and right sides of the structure are fused, and it is not allowed that one of the ring $Ar^1$ or the ring $Ar^2$ is a benzene ring and the other is a quinoline ring.

<5>

The method for producing a compound represented by General Formula (A) according to <4>, in which, in (ii) to (iv), a hydrolysis reaction is carried out after the addition reaction.

<6>

The method for producing a compound represented by General Formula (A) according to <4> or <5>, in which a solvent used in the addition reaction includes a solvent having an SP value of 21.0 $MPa^{1/2}$ or more.

<7>

Use of the compound according to any one of <1> to <3> as a synthetic intermediate of a curable monomer.

<8>

Use of the compound according to any one of <1> to <3> as a raw material compound for an optical member or a synthetic intermediate of the raw material compound.

<9>

The use according to <8>, in which the optical member is a lens.

In the present invention, in a case of a plurality of substituents, linking groups, or the like (hereinafter, referred to as a substituent or the like) represented by a specific reference or formula, or in a case of simultaneously defining a plurality of the substituent and the like, unless otherwise specified, the substituent and the like may be the same or different from each other (regardless of the presence or absence of an expression "each independently", the substituent and the like may be the same or different from each other). The same applies to the definition of the number of substituents and the like. In a case where a plurality of substituents and the like are near (particularly, adjacent to each other), unless otherwise specified, the substituents and the like may be linked to each other to form a ring. In addition, unless otherwise specified, a ring, for example, an alicyclic ring, an aromatic ring, or a heterocyclic ring may be further fused to form a fused ring.

In the present invention, unless otherwise specified, with regard to a double bond, in a case where E-form and Z-form are present in the molecule, the double bond may be any one of these forms, or may be a mixture thereof.

In addition, in the present invention, unless otherwise specified, in a case where a compound has one or two or more asymmetric carbons, for such stereochemistry of asymmetric carbons, either an (R)-form or an (S)-form can be independently taken. As a result, the compound may be a mixture of optical isomers or stereoisomers such as diastereoisomers, or may be racemic.

In addition, in the present invention, the expression of the compound means that a compound having a partially changed structure is included within a range which does not impair the effects of the present invention. Further, a compound which is not specifically described as substituted or unsubstituted may have an optional substituent within a range which does not impair the effects of the present invention.

In the present invention, with regard to a substituent (the same applies to a linking group and a ring) in which whether it is substituted or unsubstituted is not specified, within a range not impairing the desired effect, it means that the group may have an optional substituent. For example, "alkyl group" means to include both an unsubstituted alkyl group and a substituted alkyl group.

In the present invention, in a case where the number of carbon atoms in a certain group is specified, the number of carbon atoms means the number of carbon atoms in the entire group, unless otherwise specified in the present invention or the present specification. That is, in a case of a form in which the group has a substituent, it means the total number of carbon atoms including the substituent. For example, the number of carbon atoms in the "linear alkylene group" which can be adopted as $L^1$ and $L^2$ means the number of carbon atoms in a state in which a substituent is not included, as described later.

In the present invention, a numerical range represented by using "to" means a range including numerical values described before and after "to" as a lower limit value and an upper limit value.

In the present invention, each component may be used alone or in combination of two or more thereof.

In the present invention, "(meth)acrylate" represents either one or both of acrylate and methacrylate, and "(meth) acryloyl" represents either one or both of acryloyl and methacryloyl. The monomer in the present invention is distinguished from an oligomer and a polymer, and refers to a compound having a weight-average molecular weight of 1000 or less.

In the present invention, the "ethylenically unsaturated group" is used to mean including, in addition to a group represented by $CH_2═CH—$, a group in which three hydrogen atoms in $CH_2═CH—$ are substituted by substituents. The substituent which may be substituted for the three hydrogen atoms in $CH_2═CH—$ is not particularly limited as long as it does not impair the effects of the present invention, and examples thereof include an alkyl group, a cycloalkyl group, an alkoxy group, an acyl group, an acyloxy group, an alkoxycarbonyl group, a carbamoyl group, an acylamino group, an amino group, an aryl group, a halogen atom, a nitro group, and a cyano group. In addition, a group obtained by combining two or more of these groups can also be used.

In the present invention, the term aliphatic hydrocarbon group represents a group obtained by removing one optional hydrogen atom from a linear or branched alkane, a linear or branched alkene, or a linear or branched alkyne. In the present invention, the aliphatic hydrocarbon group is preferably an alkyl group obtained by removing one optional hydrogen atom from a linear or branched alkane. Examples of the alkyl group include a methyl group, an ethyl group, a propyl group, an isopropyl group, a butyl group, an isobutyl group, a sec-butyl group, a tert-butyl group, a pentyl group, a 1-methylbutyl group, a 3-methylbutyl group, a hexyl group, a 1-methylpentyl group, a 4-methylpentyl group, a heptyl group, a 1-methylhexyl group, a 5-methylhexyl group, a 2-ethylhexyl group, an octyl group, a 1-methylheptyl group, a nonyl group, a 1-methyloctyl group, a decyl group, an undecyl group, a dodecyl group, a tridecyl group, a tetradecyl group, a pentadecyl group, a hexadecyl group, a heptadecyl group, an octadecyl group, a nonadecyl group, and an eicosyl group.

In addition, in the present invention, the aliphatic hydrocarbon group (unsubstituted) is preferably an alkyl group having 1 to 12 carbon atoms, and particularly preferably a methyl group or an ethyl group.

In the present invention, the term alkyl group indicates a linear or branched alkyl group. Examples of the alkyl group include the above-described examples. The same applies to an alkyl group in a group (an alkoxy group, an alkoxycarbonyl group, an acyl group, an acyloxy group, an acylamino group, an amino group, a carbamoyl group, and the like) including the alkyl group.

In addition, in the present invention, examples of a linear alkylene group include a group obtained by removing one hydrogen atom bonded to a terminal carbon atom from a linear alkyl group among the above-described alkyl groups.

In the present invention, the term alicyclic hydrocarbon ring means a saturated hydrocarbon ring (cycloalkane). Examples of the alicyclic hydrocarbon ring include cyclopropane, cyclobutane, cyclopentane, cyclohexane, cycloheptane, cyclooctane, cyclononane, and cyclodecane.

In the present invention, the term unsaturated hydrocarbon ring means a hydrocarbon ring having a carbon-carbon unsaturated double bond, which is not an aromatic ring. Examples of the unsaturated hydrocarbon ring include indene, indane, and fluorene.

In the present invention, the term alicyclic hydrocarbon group means a cycloalkyl group obtained by removing one optional hydrogen atom from a cycloalkane. Examples of the alicyclic hydrocarbon group include a cyclopropyl group, a cyclobutyl group, a cyclopentyl group, a cyclohexyl group, a cycloheptyl group, a cyclooctyl group, a cyclononyl group, and a cyclodecyl group, and a cycloalkyl group having 3 to 12 carbon atoms is preferable.

In the present invention, a cycloalkylene group refers to a divalent group obtained by removing two optional hydrogen atoms from a cycloalkane. Examples of the cycloalkylene group include a cyclohexylene group.

In the present invention, the term aromatic ring means either one or both of an aromatic hydrocarbon ring and an aromatic heterocyclic ring.

In the present invention, the term aromatic hydrocarbon ring means an aromatic ring in which a ring is formed only by carbon atoms. The aromatic hydrocarbon ring may be a monocyclic ring or a fused ring. An aromatic hydrocarbon ring having 6 to 14 carbon atoms is preferable. Examples of aromatic hydrocarbon rings include a benzene ring, a naphthylene ring, an anthracene ring, a phenanthrene ring, and the like. In the present invention, in a case where the aromatic hydrocarbon ring is bonded to another ring, it is sufficient that the aromatic hydrocarbon ring may be substituted on another ring as a monovalent or divalent aromatic hydrocarbon ring group.

In the present invention, in a case where a monovalent group is referred to as an aromatic hydrocarbon ring group, it indicates a monovalent group obtained by removing any one hydrogen atom from an aromatic hydrocarbon ring. As the monovalent aromatic hydrocarbon ring group is preferably an aromatic hydrocarbon ring group having 6 to 14 carbon atoms, and examples of the monovalent aromatic hydrocarbon group include a phenyl group, a biphenyl group, an 1-naphthyl group, a 2-naphthyl group, an 1-anthracenyl group, a 2-anthracenyl group, a 3-anthracenyl group, a 4-anthracenyl group, a 9-anthracenyl group, an 1-phenanthryl group, a 2-phenanthryl group, a 3-phenanthryl group, a 4-phenanthryl group, and a 9-phenanthryl group. Among these, a phenyl group is preferable.

In the present invention, in a case where a divalent group is referred to as an aromatic hydrocarbon ring group, it indicates a divalent group obtained by removing any one hydrogen atom from the above-described monovalent aromatic hydrocarbon ring group. Examples of divalent aromatic hydrocarbon ring groups include a phenylene group, a naphthylene group, a phenanthrylene group, and the like, and a phenylene group is preferable and a 1,4-phenylene group is more preferable.

In the present invention, an aromatic heterocyclic ring means an aromatic ring in which a ring is formed by a carbon atom and a heteroatom. Examples of the heteroatom include an oxygen atom, a nitrogen atom, and a sulfur atom. The aromatic heterocyclic ring may be a monocyclic ring or a fused ring, and the number of atoms constituting the ring is preferably 5 to 20 and more preferably 5 to 14. The number of heteroatoms in the atoms constituting the ring is not particularly limited, but is preferably 1 to 3 and more preferably 1 or 2. Examples of the aromatic heterocyclic ring include a furan ring, a thiophene ring, a pyrrole ring, an imidazole ring, an isothiazole ring, an isoxazole ring, a pyridine ring, a pyrazine ring, a quinoline ring, a benzofuran ring, a benzothiazole ring, a benzoxazole ring, and examples of nitrogen-containing fused aromatic ring described later. In the present invention, in a case where the aromatic heterocyclic ring is bonded to another ring, it is sufficient that the aromatic heterocyclic ring may be substituted on another ring as a monovalent or divalent aromatic heterocyclic group.

In the present invention, in a case where a monovalent group is referred to as an aromatic heterocyclic group, it indicates a monovalent group obtained by removing any one hydrogen atom from an aromatic heterocyclic ring. Examples of the monovalent aromatic heterocyclic group include a furyl group, a thienyl group, a pyrrolyl group, an imidazolyl group, an isothiazolyl group, an isooxazolyl group, a pyridyl group, a pyrazinyl group, a quinolyl group, a benzofuranyl group (preferably, a 2-benzofuranyl group), a benzothiazolyl group (preferably, a 2-benzothiazolyl group), and a benzoxazolyl group (preferably, a 2-benzoxazolyl group). Among these, a furyl group, a thienyl group, a benzofuranyl group, a benzothiazolyl group, or a benzoxazolyl group is preferable, and a 2-furyl group or a 2-thienyl group is more preferable.

In the present invention, the term divalent aromatic heterocyclic group refers to a divalent group obtained by removing two optional hydrogen atoms from the aromatic heterocyclic ring, and examples thereof include a divalent group obtained by removing one optional hydrogen atom from the above-described (monovalent) aromatic heterocyclic group.

In the present invention, examples of a halogen atom include a fluorine atom, a chlorine atom, a bromine atom, and an iodine atom.

By using the compound according to the aspect of the present invention as an intermediate, it is possible to provide a high-purity curable monomer which can be used in manufacturing of an optical member such as a lens, and it is possible to increase light transmittance of a cured product.

According to the production method according to the aspect of the present invention, it is possible to produce the compound according to the aspect of the present invention with high purity and high yield.

DESCRIPTION OF THE PREFERRED EMBODIMENTS

The present invention will be described in detail. The description of configuration requirements described below may be based on representative embodiments, specific examples, and the like, but the present invention is not limited to those embodiments except as specified in the present invention.

[Compound]

A compound according to an embodiment of the present invention is a compound represented by General Formula (A) or (B), and is a carboxylic acid or carboxylic acid ester compound having a fused-ring structure.

General Formula (A)

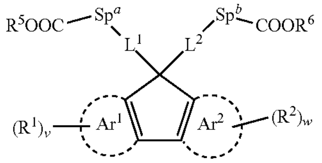

General Formula (B)

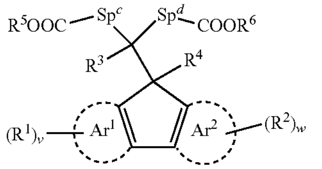

In the formulae, $R^3$ and $R^4$ represent a hydrogen atom or a monovalent substituent. $R^5$ and $R^6$ represent a hydrogen atom or an alkyl group. $L^1$ and $L^2$ represent an alkylene group having 1 to 6 carbon atoms, and $Sp^a$ to $Sp^d$ represent a single bond or a divalent linking group.

The ring $Ar^1$ represents an aromatic ring represented by Formula (AR1) or a fused ring including the aromatic ring as a ring constituting the fused ring, and the ring $Ar^2$ represents an aromatic ring represented by Formula (AR2) or a fused ring including the aromatic ring as a ring constituting the fused ring.

$R^1$ represents a substituent adopted by a ring-constituting atom of the ring $Ar^1$, and $R^2$ represents a substituent adopted by a ring-constituting atom of the ring $Ar^2$.

v is an integer of 0 or more, and a maximum number of v is a maximum number of substituents which can be adopted by the ring-constituting atom of the ring $Ar^1$.

w is an integer of 0 or more, and a maximum number of w is a maximum number of substituents which can be adopted by the ring-constituting atom of the ring $Ar^2$.

However, in General Formulae (A) and (B), a structure represented by $(R^1)_v$—$Ar^1$/cyclopentadiene skeleton/$Ar^2$—$(R^2)_w$ is not line-symmetrical. "/" represents that the two rings described on left and right sides of the structure are fused.

In addition, it is not allowed that one of the ring $Ar^1$ or the ring $Ar^2$ is a benzene ring and the other is a quinoline ring.

A compound represented by any of General Formula (A) or General Formula (B) is classified into the compound represented by General Formula (A).

As described above, one of characteristic structures of the compound represented by General Formula (A) or (B) according to the embodiment of the present invention is that a fused-ring structure represented by $(R^1)_v$—$Ar^1$/cyclopentadiene skeleton/$Ar^2$—$(R^2)_w$ does not adopt a line-symmetrical structure. Here, "/" represents that the cyclopentadiene skeleton is fused with the ring $Ar^1$ and the ring $Ar^2$. In addition, the "cyclopentadiene skeleton" means a ring structure of cyclopentadiene, excluding a substituent.

That is, the above-described definition of the compound represented by General Formula (A) or (B) means that the ring $Ar^1$ having v pieces of the substituents $R^1$ and the ring $Ar^2$ having w pieces of the substituents $R^2$, which are located on both sides of the 5-membered ring (cyclopentadiene structure), are different in at least one of the following points.

(i) mother nucleus structures of the ring $Ar^1$ and the ring $Ar^2$ (ii) substitution positions of the substituents $R^1$ and the substituents $R^2$ with respect to the mother nucleus, and (iii) structures of the substituent $R^1$ and the substituent $R^2$ Among these, it is preferable that at least the point (i) is different between the rings.

The compound according to the embodiment of the present invention is suitable, for example, as a synthetic intermediate of a curable monomer which is a raw material compound of an optical member such as a lens. A curable monomer is prepared from the compound according to the embodiment of the present invention, and in a cured product formed by using this curable monomer, the asymmetric fused-ring structural portion represented by $(R^1)_v$—$Ar^1$/cyclopentadiene skeleton/$Ar^2$—$(R^2)_w$ greatly contributes to wavelength dispersion characteristics of the refractive index.

The curable monomer obtained from the compound according to the embodiment of the present invention has the above-described asymmetric fused-ring structural portion, and a cured product formed of this monomer can achieve a sufficiently low Abbe number νD, exhibits sufficiently high θg, F values, and is suitable for use as an optical member having a chromatic aberration correction function.

Hereinafter, the substituent, the linking group, and the reference numeral in General Formula (A) or (B) will be described in detail.

(1) $L^1$ and $L^2$ $L^1$ and $L^2$ represent an alkylene group having 1 to 6 carbon atoms, and an alkylene group having 1 to 4 carbon atoms is preferable and an alkylene group having 2 or 3 carbon atoms is more preferable. The alkylene group may be linear or branched.

The number of linking atoms constituting the shortest molecular chain which links $Sp^a$ or $Sp^b$ with the 5-membered ring in which the ring $Ar^1$ and the ring $Ar^2$ are fused is preferably 1 to 6, more preferably 1 to 4, and still more preferably 2 or 3.

$L^1$ and $L^2$ are determined such that the number of carbon atoms in the alkylene group constituting $L^1$ and $L^2$ is maximized. That is, in General Formula (A), among the divalent linking groups which can be adopted as the following $Sp^a$ and $Sp^b$, the portion bonded to $L^1$ or $L^2$ is not an alkylene group.

Examples of the substituent which may be included in the alkylene group of $L^1$ and $L^2$ described above include a cycloalkyl group, an alkoxy group, an acyl group, an acyloxy group, a carbamoyl group, an acylamino group, an amino group, an aryl group, a halogen atom, a nitro group, a cyano group, and a group represented by -Sp-COOR.

Sp represents a single bond or a divalent linking group, and the description of $Sp^a$ below can be adopted. R represents a hydrogen atom or an alkyl group, and the description of $R^5$ later can be adopted.

Among these, Sp is preferably a single bond and R is preferably a hydrogen atom.

-Sp-COOR is preferably —COOR and more preferably —COOH.

As the substituent which may be included in the alkylene group of $L^1$ and $L^2$ described above, an aryl group, an alkoxy group, or a group represented by -Sp-COOR is preferable, an aryl group or a group represented by -Sp-COOR is more preferable, and an aryl group or a group represented by —COOR is still more preferable.

In a case where the alkylene group of $L^1$ and $L^2$ described above has a substituent, the number of substituents is not particularly limited, but for example, the alkylene group may have 1 to 4 substituents, preferably has 1 or 2 substituents and more preferably has 1 substituent.

It is preferable that the alkylene group of $L^1$ and $L^2$ described above does not have a substituent.

(2) $Sp^a$ and $Sp^b$ $Sp^a$ and $Sp^b$ represent a single bond or a divalent linking group.

Examples of the divalent linking group which can be adopted as $Sp^a$ or $Sp^b$ include a divalent linking group formed by bonding one or two or more groups selected from a linear alkylene group, a cycloalkylene group, a divalent aromatic hydrocarbon ring group, a divalent aromatic heterocyclic group, —O—, —S—, >C(═O), and $>NR^{201}$ The $R^{201}$ represents a hydrogen atom or an alkyl group having 1 to 3 carbon atoms.

However, among the divalent linking groups which can be adopted as the following $Sp^a$ and $Sp^b$, the portion bonded to $L^1$ or $L^2$ is not a linear alkylene group or a cycloalkylene group.

The number of carbon atoms in the above-described linear alkylene group is preferably 1 to 8, more preferably 1 to 6, still more preferably 1 to 4, and particularly preferably 1 or 2.

The number of carbon atoms in the above-described cycloalkylene group is preferably 3 to 6.

The carbon atoms in the above-described "linear alkylene group" mean the carbon number in a state without a substituent. In a case where the "linear alkylene group" has a substituent, an alkyl group can also be adopted as the substituent. In this case, the alkylene group is a branched alkylene group as a whole, but the number of linking atoms in the portion corresponding to the shortest molecular chain linking $L^1$ and $COOR^5$ or $L^2$ and $COOR^6$ in $Sp^a$ and $Sp^b$ corresponds to the number of carbon atoms in the above-described "linear alkylene group".

The carbon atoms in the above-described "cycloalkylene group" mean the carbon number in a state without a substituent.

Examples of the substituent which may be included in the linear alkylene group, the cycloalkylene group, the divalent aromatic hydrocarbon ring group, or the divalent aromatic heterocyclic group of $Sp^a$ and $Sp^b$ described above include an alkyl group, a cycloalkyl group, an alkoxy group, an acyl group, an acyloxy group, an alkoxycarbonyl group, a carbamoyl group, an acylamino group, an amino group, an aryl group, a halogen atom, a nitro group, and a cyano group, and an alkyl group or an aryl group is preferable, an alkyl group is more preferable, an alkyl group having 1 to 3 carbon atoms is still more preferable, and a methyl group is particularly preferable.

The number of substituents is not particularly limited, and for example, may be 1 to 4.

The number of the linear alkylene group, cycloalkylene group, divalent aromatic hydrocarbon ring group, divalent aromatic heterocyclic group, —O—, —S—, > C(═O), and $>NR^{201}$ constituting $Sp^a$ and $Sp^b$ which are a divalent linking group is preferably 1 to 6 and more preferably 1 to 3.

In $Sp^a$ and $Sp^b$ which are a divalent linking group, examples of the group formed by linking two or more of —O—, —S—, > C(═O), and $>NR^{201}$ include —C(═O)O—, $—NR^{201}C(═O)—$, —SC(═O)—, —OC(═O)O—, and $—NR^{201}C(═O)O—$, and —C(═O)O—, $—NR^{201}C(═O)—$, or —SC(═O)— is preferable and —C(═O)O— is more preferable.

It is sufficient that the above-described group formed by linking two or more of —O—, —S—, > C(═O), and $>NR^{201}$ constitutes $Sp^a$ and $Sp^b$ which are a divalent linking group alone or together with at least one of the linear alkylene group or the cycloalkylene group, and it is preferable that the above-described group constitutes $Sp^a$ and $Sp^b$ which are a divalent linking group together with at least one of the linear alkylene group or the cycloalkylene group.

The —C(═O)O—, $—NR^{201}C(═O)—$, $—NR^{201}C(═O)O—$, or —SC(═O)— may be disposed in a form such that either the left or right bonding site is located on the $L^1$ side or the $L^2$ side.

In $Sp^a$ and $Sp^b$, from the viewpoint of increasing a ratio of a fused structural portion consisting of the cyclopentadiene skeleton, $Ar^1$, and $Ar^2$ in the compound, in a case where $Sp^a$ or $Sp^b$ is a divalent linking group, the number of linking atoms constituting the shortest molecular chain linking $L^1$ and $COOR^5$ or $L^2$ and $COOR^6$ can be, for example, 1 to 20, and is preferably 1 to 10, more preferably 1 to 8, still more preferably 1 to 6, and particularly preferably 1 to 4. In a case where $Sp^a$ or $Sp^b$ is a single bond, the number of linking atoms constituting the shortest molecular chain linking $L^1$ and $COOR^5$ or $L^2$ and $COOR^6$ is 0, and this aspect is also preferable from the above-described viewpoint. For example, in an exemplary compound (A1-7) described later, the number of linking atoms constituting the shortest molecular chain linking $L^1$ and $COOR^5$ or $L^2$ and $COOR^6$ is 8.

As the divalent linking group which can be adopted as $Sp^a$ or $Sp^b$, a divalent linking group formed by bonding one or two or more groups selected from a linear alkylene group, a cycloalkylene group, —O—, and > C(═O) is preferable; —C(═O)O-alkylene-, —C(═O)O-cycloalkylene-, —C(═O)O-linear alkylene-OC(═O)-linear alkylene-, or —C(═O)O-linear alkylene-OC(═O)-cycloalkylene- is more preferable; and —C(═O)O-linear alkylene- is still more preferable.

As $Sp^a$ and $Sp^b$, a single bond or a divalent linking group formed by bonding one or two or more groups selected from a linear alkylene group, a cycloalkylene group, —O—, and > C(═O) is preferable; a single bond, —C(═O)O-linear alkylene-, —OC(═O)-linear alkylene-, or —C(═O)O-linear alkylene-OC(═O)-cycloalkylene- is more preferable; and a single bond is still more preferable.

$Sp^a$ and $Sp^b$ may be the same or different from each other, but it is preferable that $Sp^a$ and $Sp^b$ are the same.

(3) $Sp^c$ and $Sp^d$ $Sp^c$ and $Sp^d$ represent a single bond or a divalent linking group.

Examples of the divalent linking group which can be adopted as $Sp^c$ or $Sp^d$ include a divalent linking group formed by bonding one or two or more groups selected from a linear alkylene group, a cycloalkylene group, a divalent aromatic hydrocarbon ring group, a divalent aromatic heterocyclic group, —O—, —S—, > C(═O), and $>NR^{201}$ It is preferable that at least one of $Sp^c$ or $Sp^d$ is a divalent linking group in which a linking portion to $CR^3$ is an alkylene group.

The $R^{201}$ represents a hydrogen atom or an alkyl group having 1 to 3 carbon atoms.

The number of carbon atoms in the above-described linear alkylene group is preferably 1 to 8, more preferably 1 to 6, still more preferably 1 to 4, and particularly preferably 1 or 2.

The number of carbon atoms in the above-described cycloalkylene group is preferably 3 to 6.

The carbon atoms in the above-described "linear alkylene group" mean the carbon number in a state without a substituent. In a case where the "linear alkylene group" has a substituent, an alkyl group can also be adopted as the substituent. In this case, the alkylene group is a branched alkylene group as a whole, but the number of linking atoms in the portion corresponding to the shortest molecular chain linking $CR^3$ and $COOR^5$ or $CR^3$ and $COOR^6$ in $Sp^c$ and $Sp^d$ corresponds to the number of carbon atoms in the above-described "linear alkylene group".

The carbon atoms in the above-described "cycloalkylene group" mean the carbon number in a state without a substituent.

Examples of the substituent which may be included in the linear alkylene group, the cycloalkylene group, the divalent aromatic hydrocarbon ring group, or the divalent aromatic heterocyclic group of $Sp^c$ and $Sp^d$ described above include an alkyl group, a cycloalkyl group, an alkoxy group, an acyl group, an acyloxy group, an alkoxycarbonyl group, a carbamoyl group, an acylamino group, an amino group, a halogen atom, a nitro group, and a cyano group, and an alkyl group is preferable, an alkyl group having 1 to 3 carbon atoms is more preferable, and a methyl group is still more preferable.

The number of substituents is not particularly limited, and for example, may be 1 to 4.

The number of the linear alkylene group, cycloalkylene group, divalent aromatic hydrocarbon ring group, divalent aromatic heterocyclic group, —O—, —S—, > C(═O), and >$NR^{201}$ constituting $Sp^c$ and $Sp^d$ which are a divalent linking group is preferably 1 to 5 and more preferably 1 to 3.

In $Sp^c$ and $Sp^d$ which are a divalent linking group, examples of the group formed by linking two or more of —O—, —S—, > C(═O), and >$NR^{201}$ include —C(═O)O—, —$NR^{201}$C(═O)—, —SC(═O)—, —OC(═O)O—, and —$NR^{201}$C(═O)O—, and —C(═O)O—, —$NR^{201}$C(═O)—, or —SC(═O)— is preferable and —C(═O)O— is more preferable.

It is sufficient that the above-described group formed by linking two or more of —O—, —S—, > C(═O), and >$NR^{201}$ constitutes $Sp^c$ and $Sp^d$ which are a divalent linking group alone or together with at least one of the linear alkylene group or the cycloalkylene group, and it is preferable that the above-described group constitutes $Sp^c$ and $Sp^d$ which are a divalent linking group together with at least one of the linear alkylene group or the cycloalkylene group.

The —C(═O)O—, —$NR^{201}$C(═O)—, —$NR^{201}$C(═O)O—, or —SC(═O)— may be disposed in a form such that either the left or right bonding site is located on the $CR^3$ side.

In $Sp^c$ and $Sp^d$, from the viewpoint of increasing a ratio of a fused structural portion consisting of the cyclopentadiene skeleton, $Ar^1$, and $Ar^2$ in the compound, in a case where $Sp^a$ or $Sp^b$ is a divalent linking group, the number of linking atoms constituting the shortest molecular chain linking $CR^3$ and $COOR^5$ or $CR^3$ and $COOR^6$ can be, for example, 1 to 20, and is preferably 1 to 10, more preferably 1 to 8, still more preferably 1 to 6, and particularly preferably 1 to 4. In a case where $Sp^c$ or $Sp^d$ is a single bond, the number of linking atoms constituting the shortest molecular chain linking $CR^3$ and $COOR^5$ or $CR^3$ and $COOR^6$ is 0, and this aspect is also preferable from the above-described viewpoint. For example, in an exemplary compound (A1-5) described later, the number of linking atoms constituting the shortest molecular chain linking $CR^3$ and $COOR^5$ or $CR^3$ and $COOR^6$ is 0 for one and 1 for the other.

As the divalent linking group which can be adopted as $Sp^c$ or $Sp^d$, a divalent linking group formed by bonding one or two or more groups selected from a linear alkylene group, —O—, and > C(═O) is preferable, and a linear alkylene group is more preferable.

As $Sp^c$ and $Sp^d$, a single bond or a divalent linking group formed by bonding one or two or more groups selected from a linear alkylene group, —O—, and > C(═O) is preferable, and a single bond or a linear alkylene group is more preferable.

$Sp^c$ and $Sp^d$ may be the same or different from each other.

As $Sp^c$ and $Sp^d$, it is preferable that one of $Sp^c$ or $Sp^d$ is a single bond and the other is a linear alkylene group.

(4) $R^3$ and $R^4$ $R^3$ and $R^4$ represent a hydrogen atom or a monovalent substituent.

Examples of the monovalent substituent which may be adopted as $R^3$ and $R^4$ include an alkyl group, a cycloalkyl group, an alkoxy group, an acyl group, an acyloxy group, an alkoxycarbonyl group, a carbamoyl group, an acylamino group, an amino group, a halogen atom, a nitro group, and a cyano group, and an alkyl group is preferable.

The number of carbon atoms in the alkyl group which can be adopted as $R^3$ and $R^4$ is preferably 1 to 6, more preferably 1 to 4, and still more preferably 1 or 2.

$R^3$ and $R^4$ are preferably a hydrogen atom.

(5) $R^5$ and $R^6$ $R^5$ and $R^6$ represent a hydrogen atom or an alkyl group.

The number of carbon atoms in the alkyl group which can be adopted as $R^5$ and $R^6$ is preferably 1 to 6, more preferably 1 to 4, and still more preferably 1 or 2.

$R^5$ and $R^6$ may be the same or different from each other, but it is preferable that $R^5$ and $R^6$ are the same.

(6) Ring $Ar^1$ and Ring $Ar^2$

The ring $Ar^1$ represents an aromatic ring represented by Formula (AR1) or a fused ring including the aromatic ring as a ring constituting the fused ring, and the ring $Ar^2$ represents an aromatic ring represented by Formula (AR2) or a fused ring including the aromatic ring as a ring constituting the fused ring.

In a case where the ring $Ar^1$ and the ring $Ar^2$ are fused rings, the number of ring members in each ring constituting the fused ring is preferably 5 to 7, more preferably 5 or 6, and still more preferably 6.

In addition, in a case where the ring $Ar^1$ and the ring $Ar^2$ are fused rings, the number of rings constituting the fused ring is preferably 2 or 3, and more preferably 2. It is preferable that one of the ring $Ar^1$ or the ring $Ar^2$ is a monocyclic ring represented by Formula (AR1) or (AR2) and the other is a fused ring. The number of rings constituting this fused ring is preferably 2.

Among ring-constituting atoms constituting the fused ring, as a ring-constituting atom other than the ring represented by Formula (AR1) or (AR2), a carbon atom, an oxygen atom, a sulfur atom, or a nitrogen atom is preferable, a carbon atom or a nitrogen atom is more preferable, and a carbon atom is still more preferable.

As the ring other than the ring represented by Formula (AR1) or (AR2), which constitutes the fused ring, for example, a benzene ring or a pyridine ring is preferable.

Formula (AR1)

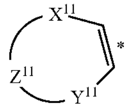

Formula (AR2)

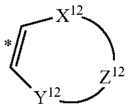

In the formulae, $X^{11}$, $Y^{11}$, $X^{12}$, and $Y^{12}$ represent an oxygen atom, a sulfur atom, a nitrogen atom, or a carbon atom.

$Z^{11}$ represents an atomic group which forms a 5- to 7-membered aromatic ring together with $—X^{11}—C{=}C—Y^{11}—$ and is composed of atoms selected from an oxygen atom, a sulfur atom, a nitrogen atom, and a carbon atom.

$Z^{12}$ represents an atomic group which forms a 5- to 7-membered aromatic ring together with $—X^{12}—C{=}C—Y^{12}—$ and is composed of atoms selected from an oxygen atom, a sulfur atom, a nitrogen atom, and a carbon atom.

* corresponds to a double bond of a cyclopentadiene ring in General Formula (A) or (B). That is, the cyclopentadiene ring is fused with the ring $Ar^1$ and the ring $Ar^2$ while sharing a side indicated by *.

($X^{11}$, $Y^{11}$, $X^{12}$, and $Y^{12}$)

The $X^{11}$, $Y^{11}$, $X^{12}$, and $Y^{12}$ represent an oxygen atom, a sulfur atom, a nitrogen atom, or a carbon atom, and a nitrogen atom or a carbon atom is preferable.

Among these, in a case where the ring $Ar^1$ described below is a monocyclic ring, it is preferable that both $X^{11}$ and $Y^{11}$ are carbon atoms, and in a case where the ring $Ar^1$ described below is a fused ring, it is preferable that both $X^{11}$ and $Y^{11}$ are nitrogen atoms or carbon atoms.

Similarly, in a case where the ring $Ar^2$ described below is a monocyclic ring, it is preferable that both $X^{12}$ and $Y^{12}$ are carbon atoms, and in a case where the ring $Ar^2$ described below is a fused ring, it is preferable that both $X^{12}$ and $Y^{12}$ are nitrogen atoms or carbon atoms.

($Z^{11}$ and $Z^{12}$)

$Z^{11}$ is an atomic group which forms a 5- to 7-membered aromatic ring together with $—X^{11}—C{=}C—Y^{11}—$ and is preferably an atomic group forming a 5- or 6-membered aromatic ring and more preferably an atomic group forming a 6-membered aromatic ring.

$Z^{12}$ is an atomic group which forms a 5- to 7-membered aromatic ring together with $—X^{12}—C{=}C—Y^{12}—$ and is preferably an atomic group forming a 5- or 6-membered aromatic ring and more preferably an atomic group forming a 6-membered aromatic ring.

$Z^{11}$ and $Z^{12}$ are an atomic group composed of atoms selected from an oxygen atom, a sulfur atom, a nitrogen atom, and a carbon atom. $Z^{11}$ and $Z^{12}$ are an atomic group composed of atoms selected from an oxygen atom, a sulfur atom, a nitrogen atom, and a carbon atom, and are preferably an atomic group including at least carbon atom and more preferably an atomic group consisting of carbon atoms.

(7) $R^1$ and $R^2$ $R^1$ represents a substituent adopted by a ring-constituting atom of the ring $Ar^1$, and $R^2$ represents a substituent adopted by a ring-constituting atom of the ring $Ar^2$. Each of $R^1$ and $R^2$ is a substituent which may be included in a nitrogen atom or a carbon atom respectively by NH or CH in a case of unsubstituted, among the ring-constituting atoms in the ring $Ar^1$ or the ring $Ar^2$.

The substituent which may be adopted as $R^1$ and $R^2$ is not particularly limited, and examples thereof include a halogen atom, an alkyl group, an acyl group, a hydroxy group, an alkoxy group, an aromatic hydrocarbon ring group, and a cyano group.

The substitution position of $R^1$ in the ring $Ar^1$ and the substitution position of $R^2$ in the ring $Ar^2$ are not particularly limited.

The number of carbon atoms in the alkyl group which can be adopted as $R^1$ and $R^2$ is preferably 1 to 5, more preferably 1 to 3, and still more preferably 1.

The number of carbon atoms in the alkoxy group which can be adopted as $R^1$ and $R^2$ is preferably 1 to 5, more preferably 1 to 3, and still more preferably 1.

The number of carbon atoms in the aromatic hydrocarbon ring group which can be adopted as $R^1$ and $R^2$ is preferably 6 to 14 and more preferably 6 to 10.

As the halogen atom which can be adopted as $R^1$ and $R^2$, a fluorine atom, a chlorine atom, or a bromine atom is preferable, and a chlorine atom is more preferable.

$R^1$ and $R^2$ are preferably a halogen atom, an alkyl group, an alkoxy group, an aromatic hydrocarbon ring group, or a cyano group, more preferably a halogen atom, an alkyl group having 1 to 5 carbon atoms, or an alkoxy group having 1 to 5 carbon atoms, and still more preferably a halogen atom, a methyl group, or a methoxy group.

(8) v and w v is an integer of 0 or more, and the maximum number of v is the maximum number of substituents which can be adopted by the ring-constituting atom of the ring $Ar^1$.

w is an integer of 0 or more, and the maximum number of w is the maximum number of substituents which can be adopted by the ring-constituting atom of the ring $Ar^2$.

v and w are preferably an integer of 0 to 4 and more preferably an integer of 0 to 2.

The total of v and w is preferably an integer of 0 to 4 and more preferably an integer of 0 to 2.

The compound according to the embodiment of the present invention is preferably the compound represented by General Formula (A) described above, and more preferably a compound represented by General Formula (A1).

General Formula (A1)

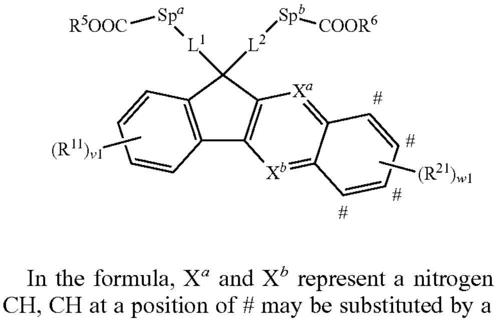

In the formula, $X^a$ and $X^b$ represent a nitrogen atom or CH, CH at a position of # may be substituted by a nitrogen atom.

$R^{11}$ and $R^{21}$ represent a substituent and v1 and w1 are an integer of 0 to 4.

$L^1$, $L^2$, $Sp^a$, $Sp^b$, $R^5$, and $R^6$ have the same meanings as $L^1$, $L^2$, $Sp^a$, $Sp^b$, $R^5$, and $R^6$ in General Formula (A), respectively.

However, in a case where one of $X^a$ or $X^b$ is a nitrogen atom, at least one of CH's at the position of # is a nitrogen atom. In addition, in a case where both $X^a$ and $X^b$ are CH, it is not allowed that only one of CH at the position of #, which is bonded to the same carbon atom as $X^a$, or CH at the position of #, which is bonded to the same carbon atom as $X^b$, is substituted by a nitrogen atom. The provision relating to these #'s means that the fused ring having $X^a$ and $X^b$ as ring-constituting atoms located on the right side of the cyclopentadiene skeleton is not a quinoline ring.

v1 and w1 are preferably an integer of 0 to 2.

As the substituent which can be adopted as $R^{11}$ and $R^{21}$, the description of the substituent which can be adopted as $R^1$ and $R^2$ described above can be applied.

$R^{21}$ is a substituent that may be included in the carbon atom in CH which may be adopted by $X^a$ and $X^b$ and the carbon atom in CH at the position of #.

In a case where $R^{11}$ or $R^{21}$ is provided, the substitution position of $R^{11}$ or $R^{21}$ is not particularly limited, but it is preferable to have $R^{11}$ or $R^{21}$ at a position represented by the following structure.

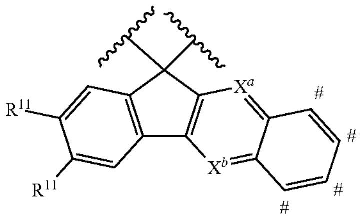

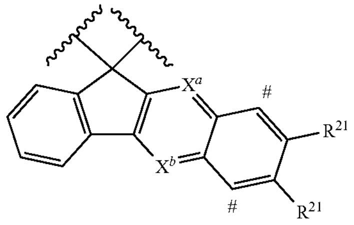

It is preferable that both $X^a$ and $X^b$ are CH or nitrogen atoms. However, in a case where both $X^a$ and $X^b$ are CH, it is not allowed that only one of CH at the position of #, which is bonded to the same carbon atom as $X^a$, or CH at the position of #, which is bonded to the same carbon atom as $X^b$, is substituted by a nitrogen atom.

In addition, it is preferable that none of CH's at the position of # is substituted by the nitrogen atom.

That is, the compound represented by General Formula (A1) is preferably a compound represented by General Formula (A1-1) or (A1-2).

General Formula (A1-1)

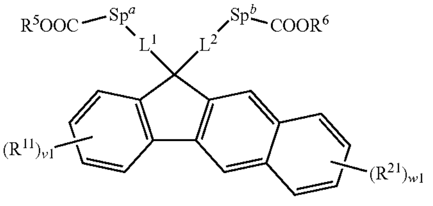

General Formula (A1-2)

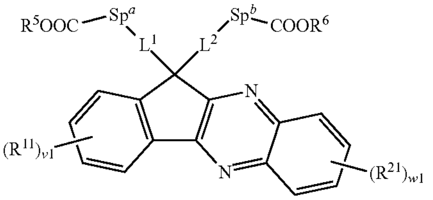

In the above formulae, $R^{11}$, $R^{21}$, $R^5$, $R^6$, $L^1$, $L^2$, $Sp^a$, $Sp^b$, v1, and w1 have the same meanings as $R^{11}$, $R^{21}$, $R^5$, $R^6$, $L^1$, $L^2$, $Sp^a$, $Sp^b$, v1, and w1 in General Formula (A1) described above.

In a case where the compound according to the embodiment of the present invention is used as an optical material, the compound according to the embodiment of the present invention is preferably a non-liquid crystalline compound. That is, from the viewpoint of using as a lens material, it is preferable that the $Sp^a$ to $Sp^d$ are linking groups having no ring structure.

Hereinafter, preferred specific examples of the compound represented by General Formula (A) or (B) are listed, but the present invention is not limited to these compounds. In the following structural formulae, Me represents a methyl group and Et represents an ethyl group.

(A1-1)

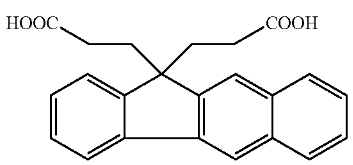

(A1-2)

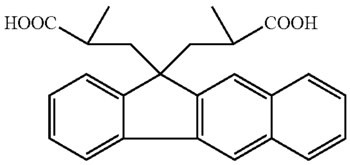

(A1-3)

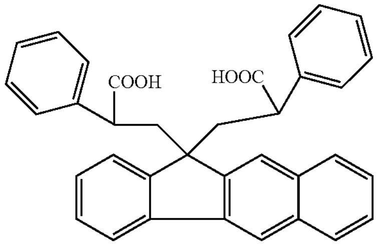

(A1-4)

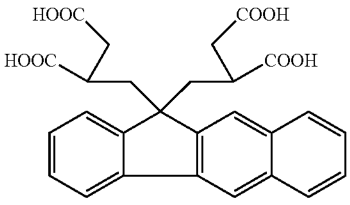

-continued
(A1-5)
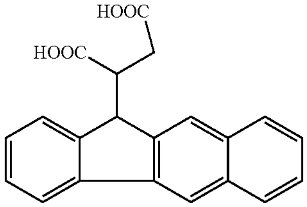
(A1-6)
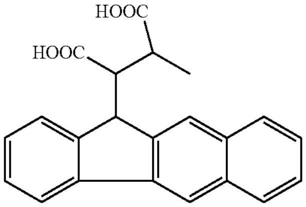
(A1-7)
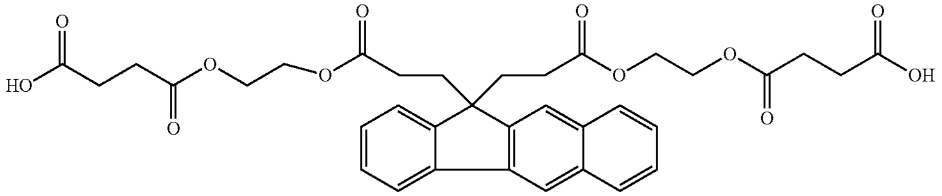
(A1-8)
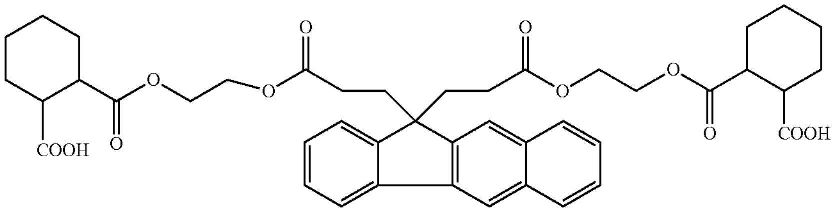
(A1-9)
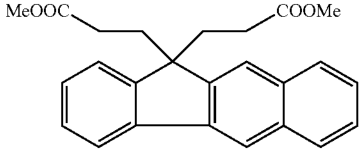
(A1-10)
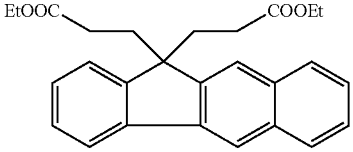
(A1-11)
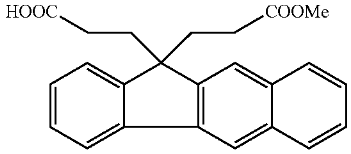
(A1-12)
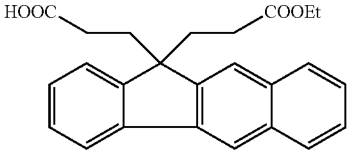
(A2-1)
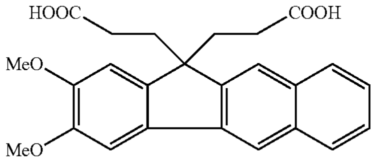
(A2-2)
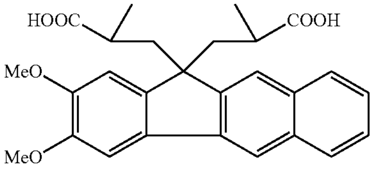
(A2-3)
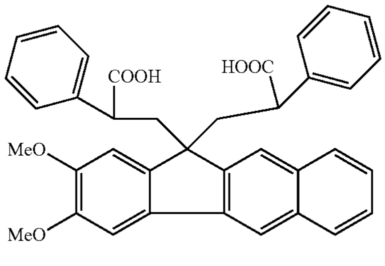
(A2-4)
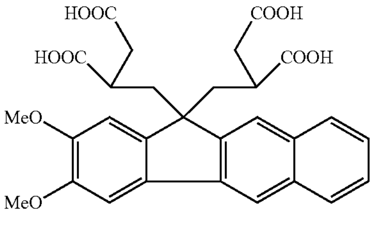
(A2-5)
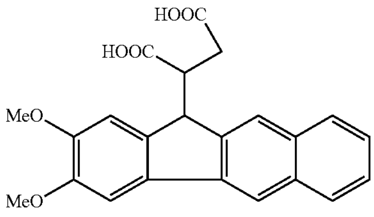
(A2-6)
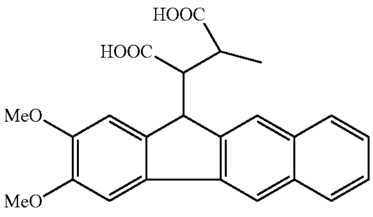

-continued
(A2-7)
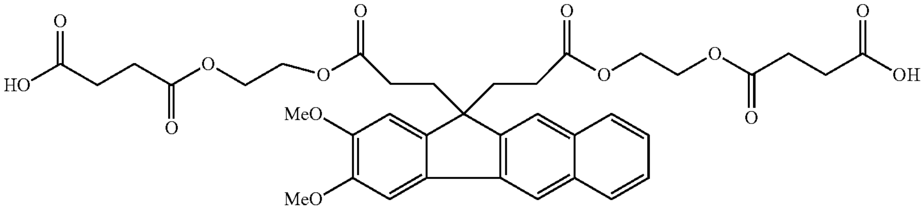
(A2-8)
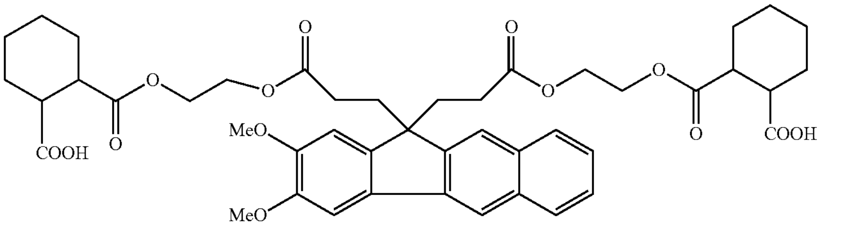
(A2-9)
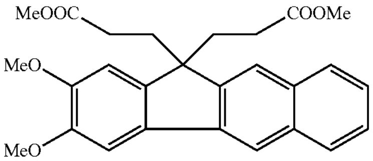
(A2-10)
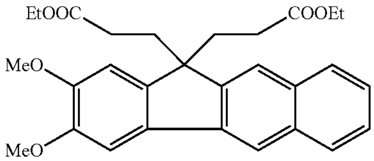
(A2-11)
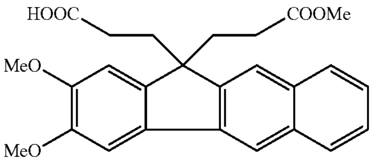
(A2-12)
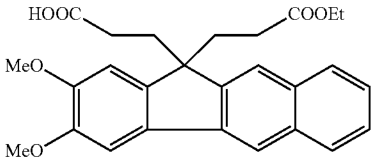
(A3-1)
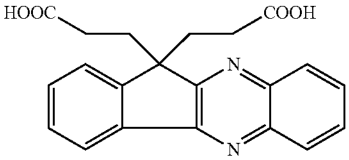
(A3-2)
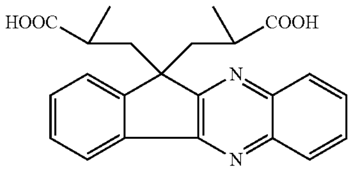
(A3-3)
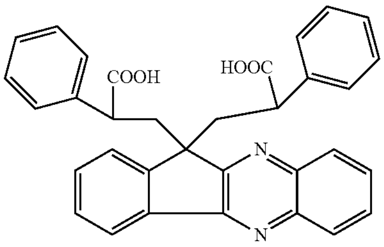
(A3-4)
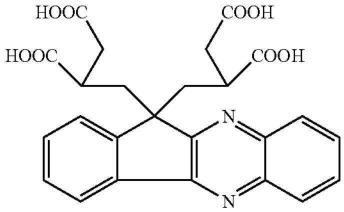
(A3-5)
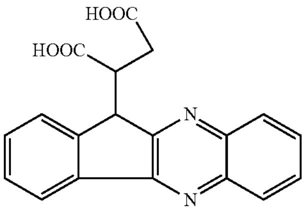
(A3-6)
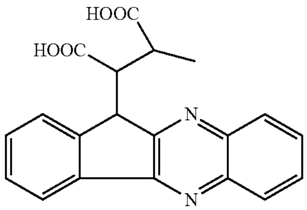

-continued
(A3-7)
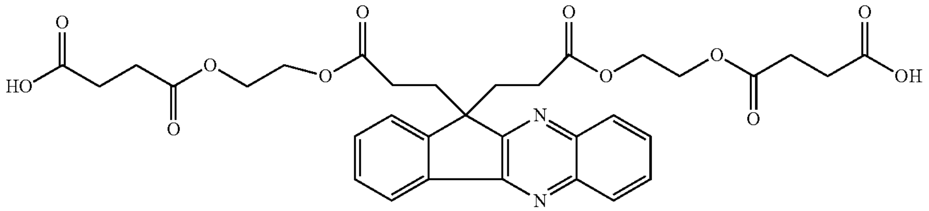
(A3-8)
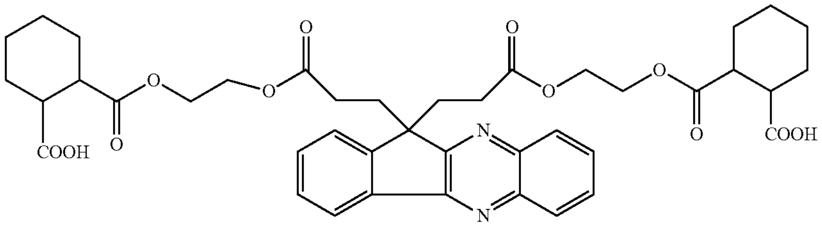
(A3-9)
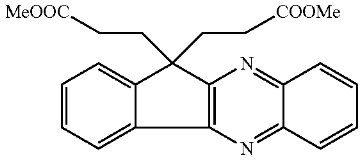
(A3-10)
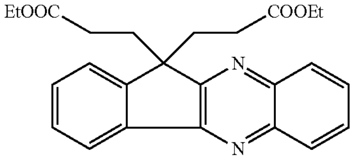
(A3-11)
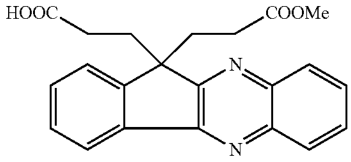
(A3-12)
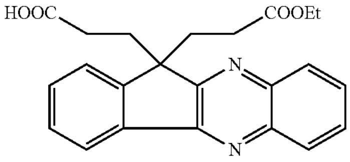
(A4-1)
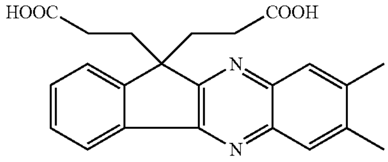
(A4-2)
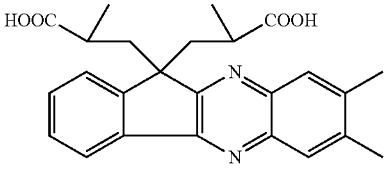
(A4-3)
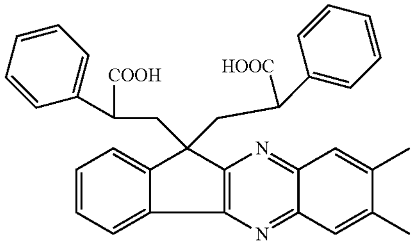
(A4-4)
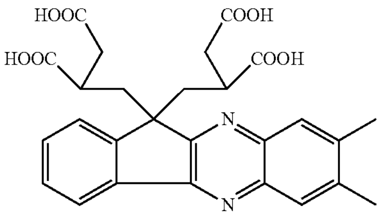
(A4-5)
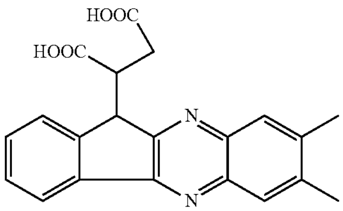
(A4-6)
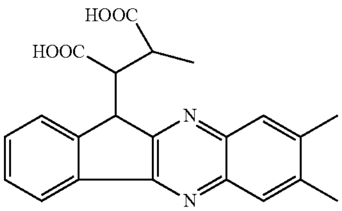

-continued
(A4-7)
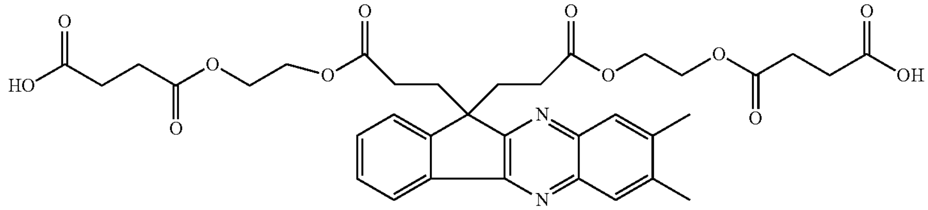
(A4-8)
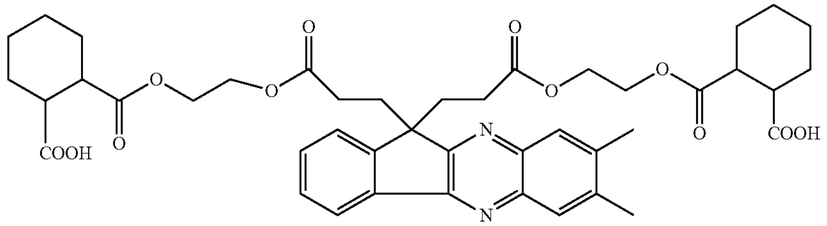
(A4-9)
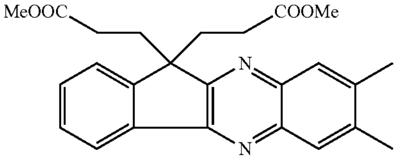
(A4-10)
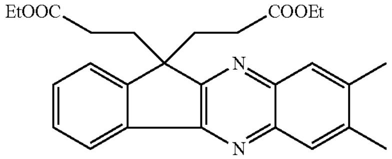
(A4-11)
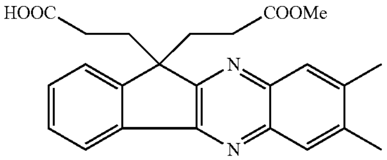
(A4-12)
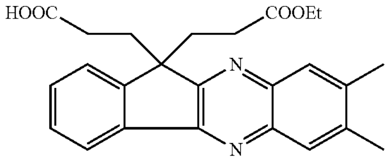
(A5-1)
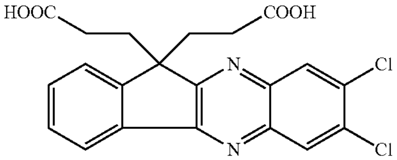
(A5-2)
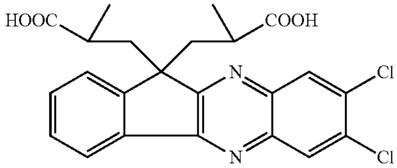
(A5-3)
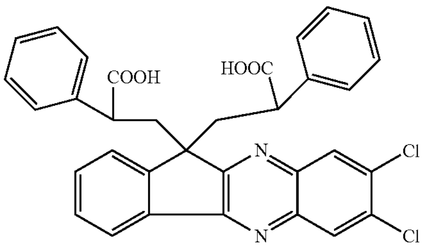
(A5-4)
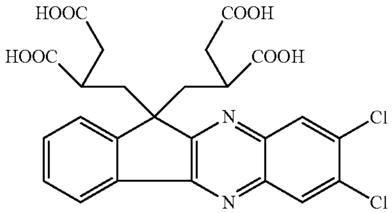
(A5-5)
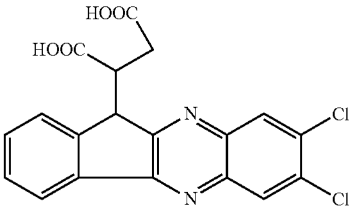
(A5-6)
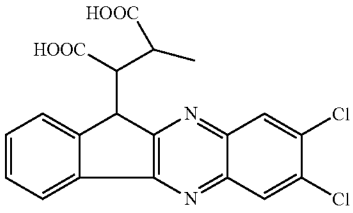

-continued
(A5-7)
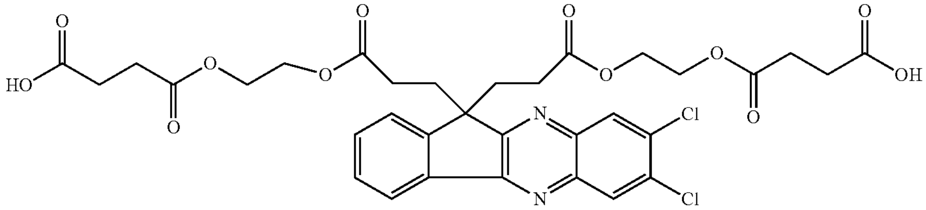
(A5-8)
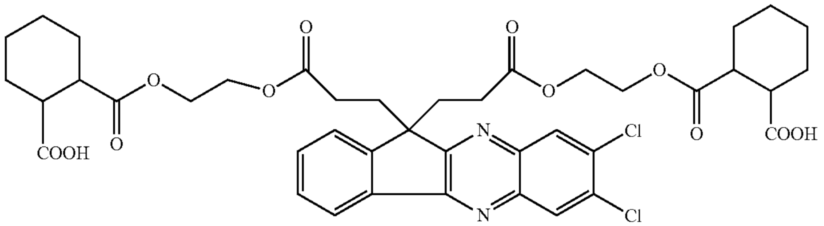
(A5-9)
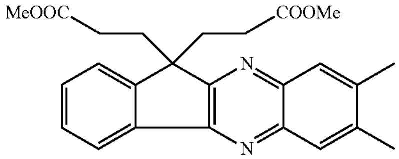
(A5-10)
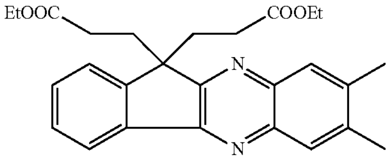
(A5-11)
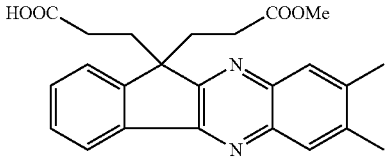
(A5-12)
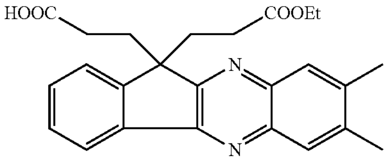
(A6-1)
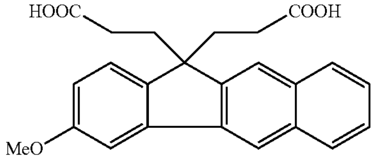
(A7-1)
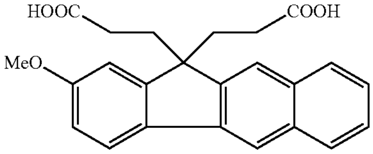
(A8-1)
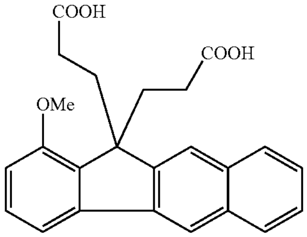
(A9-1)
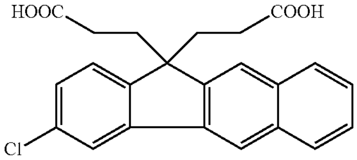
(A10-1)
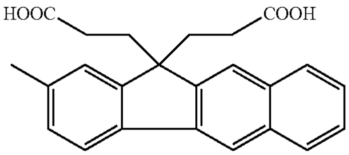
(A11-1)
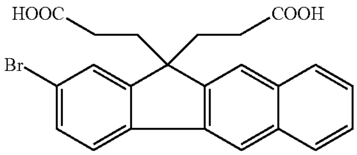
(A12-1)
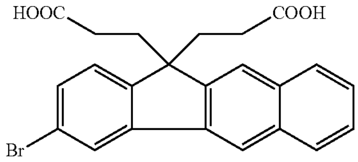
(A13-1)
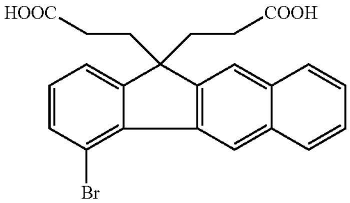

-continued
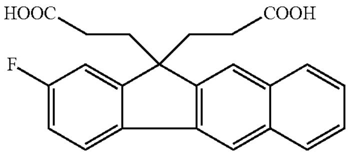
(A14-1)
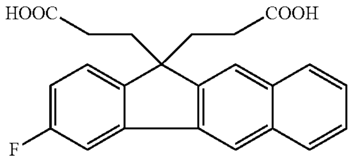
(A15-1)
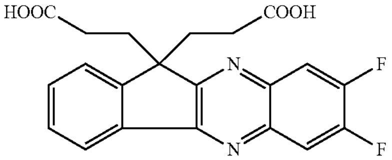
(A16-1)
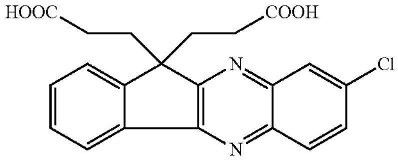
(A17-1)
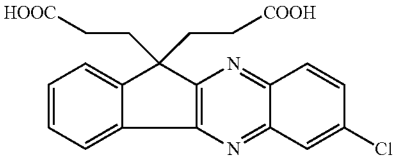
(A18-1)
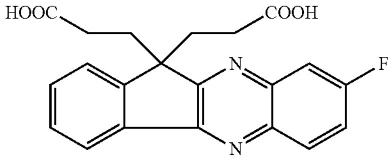
(A19-1)
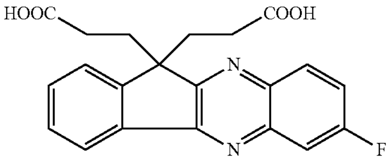
(A20-1)
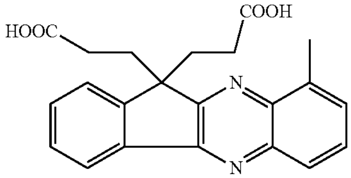
(A21-1)
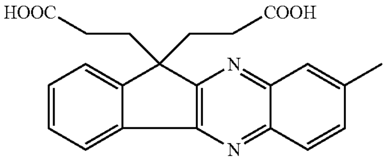
(A22-1)
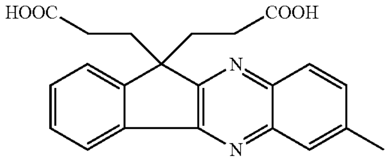
(A23-1)
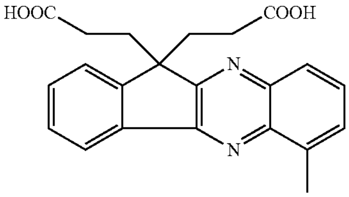
(A24-1)
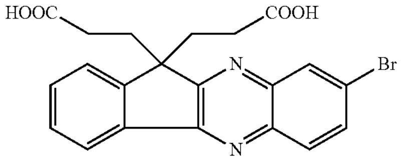
(A25-1)
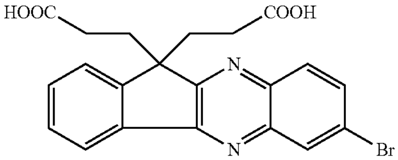
(A26-1)
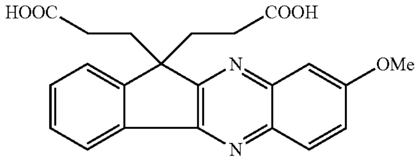
(A27-1)
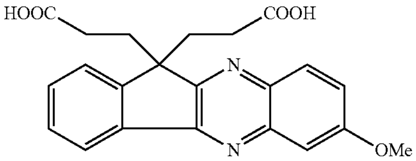
(A28-1)

The compound according to the embodiment of the present invention has a high reaction rate in its synthesis, and can be obtained as a high-purity product without going through a purification step. In consideration of the use of the raw material compound of an optical member or an intermediate thereof, a transmittance of the compound according to the embodiment of the present invention is preferably 97.0% or more, more preferably 98.0% or more, and still more preferably 99.0% or more.

The above-described transmittance means a transmittance at 420 nm, which is measured by a method described in Examples later. In a case of preparing a solution of the compound, the compound may be dissolved in a solvent which is soluble the compound.

A purity of the compound according to the embodiment of the present invention is preferably 89.0% or more, more preferably 90.0% or more, still more preferably 93.0% or more, and particularly preferably 95.0% or more.

The above-described purity means an HPLC purity measured by a method described in Examples later.

[Use of Compound]

The compound according to the embodiment of the present invention can be used as a raw material for various functional materials or a synthetic intermediate thereof as a novel compound by itself.

In addition, for example, a polymerizable group such as a (meth)acryloyl group, an epoxy group, and a vinyl group can be introduced into the compound according to the embodiment of the present invention through a carboxy group, and the compound according to the embodiment of the present invention is suitable as a synthetic intermediate of a curable monomer.

As shown in Examples described later, a cured product made from a curable monomer derived from the compound represented by General Formula (A) or (B) according to the embodiment of the present invention can achieve both a low Abbe number and a high transmittance at a high level, and also has a high partial dispersion ratio θg, F and excellent wavelength dispersion characteristics of the refractive index. Therefore, the compound can be used as a raw material compound of an optical member or a synthetic intermediate thereof, and can be preferably used as an optical member such as a lens or an optical film.

In the present invention, an Abbe number (νD) and a partial dispersion ratio (θg, F) of the cured product are values measured by the methods described in Examples later.

The Abbe number νD of the cured product is preferably 22.0 or less, more preferably 21.0 or less, and still more preferably 20.0 or less. In addition, the lower limit value of the Abbe number of the cured product is not particularly limited, but it is preferably 1 or more, more preferably 3 or more, still more preferably 5 or more, and particularly preferably 7 or more.

The partial dispersion ratio (θg, F) of the cured product is not particularly limited, but is preferably 0.65 or more, more preferably 0.70 or more, still more preferably 0.75 or more, and from the viewpoint of being particularly suitably used as a lens resin having high chromatic aberration correction power in a blue region, particularly preferably 0.80 or more. In addition, the upper limit value of the partial dispersion ratio (θg, F) of the cured product is not particularly limited, but it is preferably 2.0 or less, more preferably 1.8 or less, and still more preferably 1.7 or less.

In addition, the transmittance of the cured product is a transmittance at a wavelength of 420 nm, which is measured by a method described in Examples later, and is a value of an external transmittance including surface reflection.

A transmittance of the cured product is preferably 65.0% or more, more preferably 70.0% or more, and still more preferably 80.0% or more. The upper limit value of the transmittance of the cured product is not particularly limited, but is practically 89% or less.

The compound according to the embodiment of the present invention can be easily obtained as a compound having high purity and high transmittance by, for example, a production method described below. In addition, by using, as the solvent used in the reaction, a solvent including a solvent showing a specific SP value, the compound can be obtained in a higher yield and higher purity. Therefore, by using the compound according to the embodiment of the present invention, it is possible to further improve optical characteristics of the obtained optical member.

[Method for Producing Compound]

In a production method according to an embodiment of the present invention, a carboxylic acid or carboxylic acid ester compound represented by General Formula (A) or (B) described above can be produced by subjecting (i) an ethylenically unsaturated carboxylic acid compound, (ii) an ethylenically unsaturated carboxylic acid ester compound, (iii) an ethylenically unsaturated dicarboxylic acid anhydride, or (iv) an alkylcarboxylic acid ester compound having a leaving group at a 0-position to an addition reaction with a compound represented by General Formula (S) in the presence of a base.

In a case where one equivalent of (i) the ethylenically unsaturated carboxylic acid compound, (ii) the ethylenically unsaturated carboxylic acid ester compound, (iii) the ethylenically unsaturated dicarboxylic acid anhydride, or (iv) the alkylcarboxylic acid ester compound having a leaving group at the ω-position is introduced into the compound represented by General Formula (S), the compound represented by General Formula (B) is obtained, and in a case where two equivalents thereof are introduced into the compound represented by General Formula (S), the compound represented by General Formula (A) is obtained.

Among these, the production method according to the embodiment of the present invention is suitably used for producing the above-described compound represented by General Formula (A).

General Formula (S)

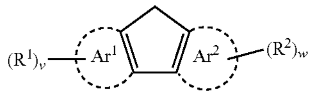

The ring $Ar^1$, the ring $Ar^2$, $R^1$, $R^2$, v, and w in the formula have the same meanings as the ring $Ar^1$, the ring $Ar^2$, $R^1$, $R^2$, v, and w in General Formula (A) or (B) described above.

Reagents, solvents, reaction conditions, and the like used for the above-described addition reaction will be described.

(Compound Represented by General Formula (S))

The above-described compound represented by General Formula (S) is preferably a compound represented by General Formula (SA1), and more preferably a compound represented by General Formula (SA1-1) or (SA1-2).

General Formula (SA1)

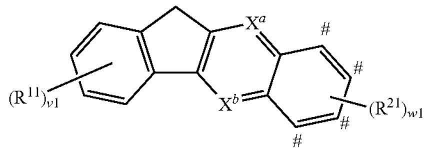

$R^{11}$, $R^{21}$, $X^a$, $X^b$, v1, w1, and # in the formula have the same meanings as $R^{11}$, $R^{21}$, $X^a$, $X^b$, v1, w1, and # in General Formula (A1) described above.

General Formula (SA1-1)

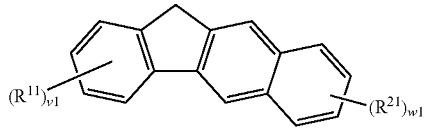

General Formula (SA1-2)

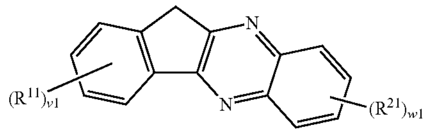

$R^{11}$, $R^{21}$, v1 and w1 in the formulae have the same meanings as $R^{11}$, $R^{21}$, v1, and w1 in General Formula (A1) described above.

A method for obtaining the above-described compound represented by General Formula (S) is not particularly limited, and the compound represented by General Formula (S) may be obtained commercially or may be obtained by synthesis. In a case of being obtained by synthesis, a method for producing (method for synthesizing) the compound represented by General Formula (S) is not particularly limited, and the compound represented by General Formula (S) can be synthesized by a conventional method or with reference to a method described in Examples.

For example, by reacting a carbonyl compound represented by General Formula (s) with triethylsilane in the presence of a metal catalyst or a Lewis acid such as a boron trifluoride-diethyl ether complex, a carbonyl group (>C═O) can be reduced to methylene (—$CH_2$—) to obtain the above-described represented by General Formula (S). $Ar^1$, $Ar^2$, $R^1$, $R^2$, v, and w in General Formula (s) have the same meanings as $Ar^1$, $Ar^2$, $R^1$, $R^2$, v, and w in General Formula (S).

General Formula (s)

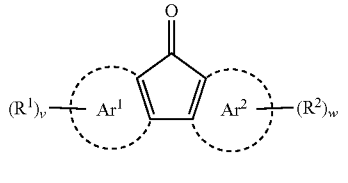

(Reactant)

By reacting the compound represented by General Formula (S) with (i) the ethylenically unsaturated carboxylic acid compound or (iii) the ethylenically unsaturated dicarboxylic acid anhydride, the carboxylic acid compound represented by General Formula (A) or (B) (that is, among the compounds represented by General Formula (A) or (B), a compound in which $R^5$ and $R^6$ are hydrogen atoms) is obtained. However, in a case of using (iii) the ethylenically unsaturated dicarboxylic acid anhydride, a hydrolysis reaction is carried out after the addition reaction.

In addition, by reacting the compound represented by General Formula (S) with (ii) the ethylenically unsaturated carboxylic acid ester compound or (iv) the alkylcarboxylic acid ester compound having a leaving group at the ω-position, the carboxylic acid ester compound represented by General Formula (A) or (B) (that is, among the compounds represented by General Formula (A) or (B), a compound in which $R^5$ and $R^6$ are alkyl groups) is obtained. In a case of using (ii) the ethylenically unsaturated carboxylic acid ester compound or (iv) the alkylcarboxylic acid ester compound having a leaving group at the ω-position, by further carrying out a hydrolysis reaction after the addition reaction, the corresponding carboxylic acid compound (that is, among the compounds represented by General Formula (A) or (B), a compound in which $R^5$ and $R^6$ are hydrogen atoms) is obtained.

The hydrolysis reaction with (ii) to (iv) above can be carried out according to a conventional method without any particular limitation.

The number of ethylenically unsaturated groups in each compounds of (i) to (iv) is not particularly limited, but is preferably 1.

The above-described (i) ethylenically unsaturated carboxylic acid compound means a carboxylic acid compound having an ethylenically unsaturated group.

The number of carboxy groups in the above-described (i) ethylenically unsaturated carboxylic acid compound is not particularly limited, and may be, for example, 1 to 4, preferably 1 or 2. In a case of obtaining the compound represented by General Formula (B), the above-described compound (i) is a compound in which at least two of substituents on two carbon atoms constituting a carbon-carbon double bond in the ethylenically unsaturated group (four substituents in total) have carboxy groups.

Examples of the above-described (i) ethylenically unsaturated carboxylic acid compound include (meth)acrylic acid, maleic acid, itaconic acid, citraconic acid, and dermal acid.

The above-described (ii) ethylenically unsaturated carboxylic acid ester compound means a carboxylic acid ester compound having an ethylenically unsaturated group, and specifically, is a compound having an ethylenically unsaturated group and an alkoxycarbonyl group.

The number of alkoxycarbonyl groups in the above-described (ii) ethylenically unsaturated carboxylic acid ester compound is not particularly limited, and may be, for example, 1 to 4, preferably 1 or 2. In a case of obtaining the compound represented by General Formula (B), the above-described compound (ii) is a compound in which at least two of substituents on two carbon atoms constituting a carbon-carbon double bond in the ethylenically unsaturated group (four substituents in total) are a substituent including an alkoxycarbonyl group.

Examples of the above-described (ii) ethylenically unsaturated carboxylic acid ester compound include an alkyl ester compound of (i) the ethylenically unsaturated carboxylic acid compound mentioned above.

The above-described (iii) ethylenically unsaturated dicarboxylic acid anhydride means an anhydride of dicarboxylic acid having an ethylenically unsaturated group.

The number of dicarboxylic anhydride structures in the above-described (iii) ethylenically unsaturated dicarboxylic acid anhydride is not particularly limited, and may be, for example, 1 or 2, preferably 1. A position of the ethylenically unsaturated group in the compound is not particularly limited, and the compound may have a 5- or 6-membered ring atomic group including an acid anhydride structure (—OC(═O)O—) as a ring-constituting atomic group, or may have the acid anhydride structure as a substituent on a 5- or 6-membered ring including the acid anhydride structure as a ring-constituting atomic group.

Among the above-described (iii) ethylenically unsaturated dicarboxylic acid anhydrides, examples of the compound having a carbon-carbon double bond in the ethylenically unsaturated group as the 5- or 6-membered ring atomic group including the acid anhydride structure as a ring-constituting atomic group include a maleic acid anhydride and a citraconic acid anhydride, and examples of the compound having, as a substituent, a 5- or 6-membered ring including the acid anhydride structure as a ring-constituting atomic group include itaconic acid anhydride.

The above-described (iv) alkylcarboxylic acid ester compound having a leaving group at the w-position means an alkylcarboxylic acid ester compound having a leaving group such as a halogen atom at the ω-position. That is, the above-described compound (iv) has an alkoxycarbonyl group and has a leaving group on the carbonyl group side in the ester bond. In a case of obtaining the compound represented by General Formula (B), the above-described compound (iv) is a compound in which a carbon atom at the ω-position, which has the leaving group, further has a substituent including another alkoxycarbonyl group.

Examples of the leaving group include a halogen atom, a C1 to C6 alkylsulfonyloxy group, and an arylsulfonyloxy group. C1 to C6 indicate that the number of carbon atoms is 1 to 6.

Examples of the above-described (iv) alkylcarboxylic acid ester compound having a leaving group at the ω-position include ethyl chloroacetate, ethyl bromoacetate, tert-butyl chloroacetate, tert-butyl bromoacetate, ethyl 3-bromopropionate, and ethyl 4-bromobutyrate.

Examples of a reference example of the method of obtaining the carboxylic acid ester compound represented by General Formula (A) or (B) by the reaction of the above-described compound represented by General Formula (S) with the above-described (iv) alkylcarboxylic acid ester compound having a leaving group at the ω-position include the synthesis method described in [0078] and [0162] of WO2014/050738A (JP5682094B) and the like.

The above-described (i) ethylenically unsaturated carboxylic acid compound, (ii) ethylenically unsaturated carboxylic acid ester compound, (iii) ethylenically unsaturated dicarboxylic acid anhydride, or (iv) alkylcarboxylic acid ester compound having a leaving group at the ω-position may have a substituent as long as it does not affect the above-described addition reaction.

In a case of producing the above-described compound represented by General Formula (A), the amount of the above-described (i) ethylenically unsaturated carboxylic acid compound, (ii) ethylenically unsaturated carboxylic acid ester compound, (iii) ethylenically unsaturated dicarboxylic acid anhydride, or (iv) alkylcarboxylic acid ester compound having a leaving group at the w-position used may be 2 to 10 mol, preferably 2.2 to 6 mol with respect to 1 mol of the above-described compound represented by General Formula (S).

In a case of producing the above-described compound represented by General Formula (B), the amount of the above-described (i) ethylenically unsaturated carboxylic acid compound, (ii) ethylenically unsaturated carboxylic acid ester compound, (iii) ethylenically unsaturated dicarboxylic acid anhydride, or (iv) alkylcarboxylic acid ester compound having a leaving group at the w-position used may be 1 to 10 mol, preferably 1.1 to 6 mol with respect to 1 mol of the above-described compound represented by General Formula (S).

(Base)

Examples of the base used in the above-described addition reaction include quaternary ammonium salts such as benzyltrimethylammonium hydroxide and benzyltriethylammonium hydroxide, and alkoxides of alkali metals, such as sodium methoxide, sodium ethoxide, and potassium tert-butoxide. In addition, two or more kinds thereof can also be used in combination.

The amount of the above-described base used may be 1 to 100 mol %, preferably 5 to 50 mol % with respect to the above-described compound represented by General Formula (S). For example, the use of 100 mol % of the base means that 1 mol of the base is used with respect to 1 mol of the above-described compound represented by General Formula (S).

In a case where the above-described quaternary ammonium salt and the above-described alkoxide of alkali metal are used in combination, a ratio thereof is preferably 0.1 to 5 mol of the alkoxide of alkali metal per 1 mol of the quaternary ammonium salt.

(Solvent)

As the solvent used in the above-described addition reaction, an ester-based solvent, an amide-based solvent, a nitrile-based solvent, a sulfoxide-based solvent, or the like can be suitably used.

In particular, it is preferable to use at least one kind or more of a solvent having an SP value of 21.0 $MPa^{1/2}$ or more. Examples of the solvent having an SP value of 21.0 $MPa^{1/2}$ or more include N,N-dimethylformamide (SP value: 24.8), N,N-dimethylacetamide (SP value: 22.7), N-methylpyrrolidone (SP value: 22.9), acetonitrile (SP value: 24.6), propionitrile (SP value: 21.7), and dimethyl sulfoxide (SP value: 26.6). The unit of the SP value in parentheses is $MPa^{1/2}$.

The SP value of the above-described solvent is a value described in Polymer Handbook $4^{th}$ edition.

By using a solvent having an SP value of 21.0 $MPa^{1/2}$ or more as the solvent used in the above-described addition reaction, a reaction rate of the addition reaction can be increased, and the target carboxylic acid or carboxylic acid ester compound represented by General Formula (A) or (B) can be obtained with high purity.

A proportion of the solvent having an SP value of 21.0 $MPa^{1/2}$ or more in the solvent used in the above-described addition reaction is not particularly limited as long as the reaction rate of the addition reaction can be increased. For example, the above-described proportion can be 10% by mass or more, preferably 25% by mass or more, more preferably 50% by mass or more, and still more preferably 75% by mass or more.

The amount of the above-described solvent used may be 1 to 20 times (v/w), preferably 3 to 17 times (v/w) and more preferably 5 to 15 times (v/w) with respect to the above-described compound represented by General Formula (S).

v/w means a volume milliliter of the solvent with respect to a mass gram of the above-described compound represented by General Formula (S).

In addition to the solvent mentioned above, a solvent used as a diluting solution for the reagents, such as an alcohol-based solvent, may be contained in the reaction system for carrying out the above-described addition reaction. However, the solvent is not included in the above-described calculation of the amount of the solvent used.

(Reaction Conditions)

The reaction conditions of the above-described addition reaction are not particularly limited, but for example, a reaction temperature can be set to 0° C. to 100° C., preferably 20° C. to 80° C., and a reaction time can be set to 0.5 to 10 hours, preferably 0.5 to 5 hours.

After completion of the above-described addition reaction, a treatment method differs depending on whether the product has a carboxy group (that is, $R^5$ and $R^6$ in General Formula (A) or (B) are hydrogen atoms) or an alkoxycarbonyl group (that is, $R^5$ and $R^6$ in General Formula (A) or (B) are alkyl groups).

In a case of having a carboxy group, a caustic alkaline aqueous solution such as sodium hydroxide is added to the reaction solution to dilute the reaction solution, the product is dissolved in an alkaline aqueous solution, and this aqueous solution is washed with an appropriate solvent such as ethyl acetate or toluene. Subsequently, hydrochloric acid is added to the separated water phase to acidify the water phase, thereby liberating a compound having a carboxy group. The liberated compound having a carboxy group is separated by filtration, washed thoroughly with distilled water, and then dried to obtain the target compound having a carboxy group.

On the other hand, in a case of a compound having an alkoxycarbonyl group, a mineral acid such as hydrochloric acid is added to the reaction solution to neutralize the compound, and the product is extracted into an appropriate solvent such as ethyl acetate. The solvent phase is washed with distilled water, and the solvent is distilled off to obtain a product having a carboxylic acid ester group. As necessary, the obtained product may be recrystallized from an alcohol-based solvent such as methanol and isopropyl alcohol to further increase the purity.

EXAMPLES

Hereinafter, the present invention will be described in more detail based on Examples. The materials, reagents, amounts used and proportions thereof, treatment details, treatment procedures, and the like described in the following examples can be appropriately modified as long as the gist of the invention is maintained. Therefore, the scope of the present invention should not be construed as being limited to the following specific examples.

SYNTHESIS EXAMPLE

The compound represented by General Formula (A) or (B) was synthesized as follows.

In the following synthesis route, THF represents tetrahydrofuran, Et represents an ethyl group, w/v % means weight to volume percentage (weight/volume %), and room temperature means 25° C.

An HPLC measurement and a transmittance measurement were carried out according to measuring methods shown below.

(HPLC Measurement)

Using a high-speed liquid chromatography (product name: SPD-10AV VP) manufactured by Shimadzu Corporation, a purity of the compound was measured under the following conditions. In a case where the compound was added to a solvent, a peak derived from the solvent was subtracted, and then the HPLC purity was obtained.

Column: TSKgel ODS-100Z 5 μm (4.6 mmφ×150 mm) (manufactured by Tosoh Corporation)

Column temperature: 40° C.

Eluent: acetonitrile:pure water:phosphoric acid (volume ratio)=700:300:1

Flow Rate: 1.0 ml/min

Detection wavelength: 254 nm

Injection amount: 10 μL

Sample: compound was dissolved in the eluent so as to have a concentration of 5 mg/50 ml.

(Measurement of Transmittance)

Using a spectrophotometer (product name: UV-2550) manufactured by Shimadzu Corporation, a transmittance of the compound at a wavelength of 420 nm was measured under the following conditions. As the transmittance at 420 nm is higher, coloration is less likely to occur.

Cell: square quartz cell (optical path length: 1 cm)

Sample: compound was dissolved in THF so as to have a concentration of 50 mg/5 mL.

Blank: THF (solvent)

[Synthesis of Compounds (SA-1) to (SA-5)]

<Synthesis of Compound (SA-1)>

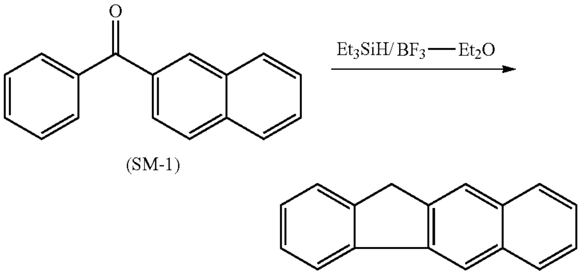

(SM-1)

(SA-1)

15.0 g of 11H-benzo[b]fluoren-11-one (SM-1) and 60 mL of methylene chloride were charged into a 500 mL three-neck flask, and 60 mL of trifluoroacetic acid and 22.8 g of triethylsilane were added thereto while cooling the mixture in an ice bath. Subsequently, 18.6 g of a boron trifluoride-diethyl ether complex was added dropwise thereto over 30 minutes, and then the reaction was carried out at 40° C. for 3 hours. After cooling to room temperature, 180 mL of cyclopentylmethyl ether was added thereto, and the mixture was further stirred for 2 hours. The precipitated solid was recovered by filtration and vacuum-dried in a vacuum oven to obtain 10.3 g of a compound (SA-1) (yield: 73.1%).

<Synthesis of Compound (SA-2)>

7.2 g of a compound (SA-2) (yield: 82.0%) was obtained in the same manner as in the above-described synthesis of the compound (SA-1), except that the compound (SM-1) was changed to a compound (SM-2).

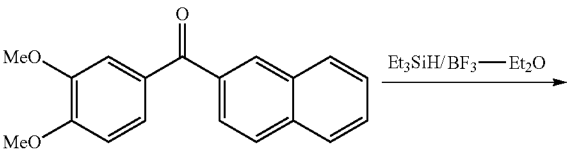

(SM-2)

-continued

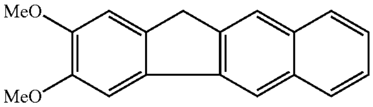

(SA-2)

<Synthesis of Compound (SA-3)>

6.0 g of a compound (SA-3) (yield: 63.8%) was obtained in the same manner as in the above-described synthesis of the compound (SA-1), except that the compound (SM-1) was changed to a compound (SM-3).

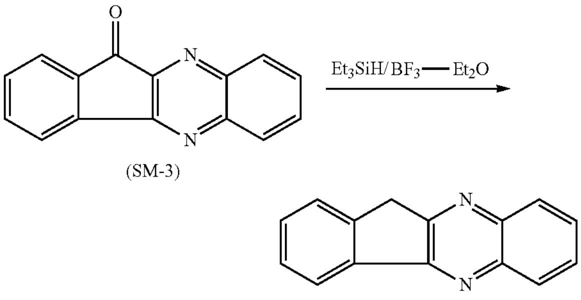

(SM-3)

(SA-3)

<Synthesis of Compound (SA-4)>

6.2 g of a compound (SA-4) (yield: 66.0%) was obtained in the same manner as in the above-described synthesis of the compound (SA-1), except that the compound (SM-1) was changed to a compound (SM-4).

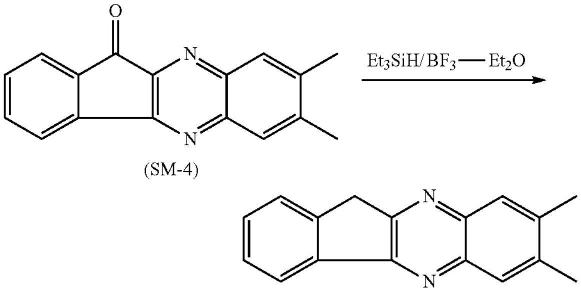

(SM-4)

(SA-4)

<Synthesis of Compound (SA-5)>

8.2 g of a compound (SA-5) (yield: 86.5%) was obtained in the same manner as in the above-described synthesis of the compound (SA-1), except that the compound (SM-1) was changed to a compound (SM-5).

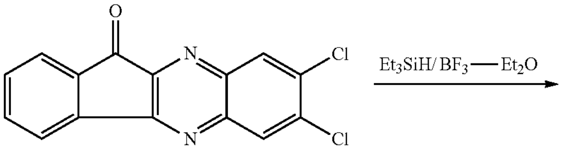

(SM-5)

-continued

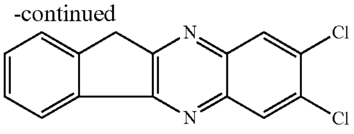

(SA-5)

Synthesis Example 1: Synthesis of Compound (A1-1)

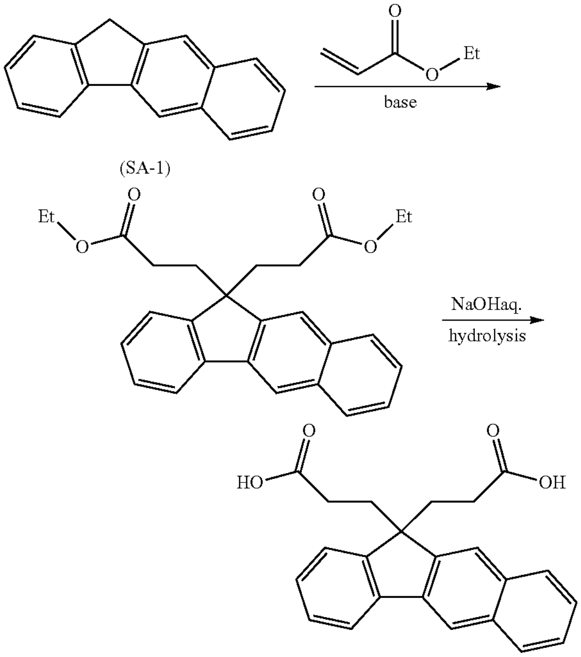

(SA-1)

(A1-1)

5.0 g (23 mmol) of the compound (SA-1), 6.9 g (69 mmol) of ethyl acrylate, and 50 mL of N,N-dimethylacetamide were charged into a 200 mL three-neck flask, and stirred at room temperature for 10 minutes. 2.9 g of a 40% by mass methanol solution of benzyltrimethylammonium hydroxide (0.69 mmol of benzyltrimethylammonium hydroxide) was added thereto, and the mixture was reacted at 80° C. for 1 hour. After confirming disappearance of the raw material compound (SA-1) by thin-layer chromatography (TLC), 7.5 mL of water and 7.5 mL of a 50 w/v % sodium hydroxide aqueous solution were added thereto, and the mixture was stirred at 80° C. for 1 hour to hydrolyze ethyl ester. After cooling to room temperature, the mixture was neutralized with 6N hydrochloric acid, ethyl acetate was added thereto, and a liquid separation operation was performed. The organic layer was washed with 1N hydrochloric acid and saturated saline, and dried with magnesium sulfate. After removing the magnesium sulfate by filtration, the solvent was concentrated, and the precipitated solid was dispersed and washed with a mixed solvent of ethyl acetate and hexane to obtain 4.8 g of a compound (A1-1) (yield: 58%). An area % of the compound (A1-1) determined from the HPLC measurement was 96.6%, and the area of the raw material compound (SA-1) was 0.1% or less. In addition, the transmittance of the compound (A1-1) at 420 nm was 99.3%.

$^1$H-NMR data of compound (A1-1) (400 MHz, DMSO-$d_6$): δ 1.35 to 1.45 ppm (m, 4H), 2.35 to 2.45 ppm (m, 4H), 7.35 to 7.60 ppm (m, 5H), 7.90 to 8.10 ppm (m, 4H), 8.35 ppm (s, 1H), 11.9 ppm (s, 2H)

Synthesis Example 2: Synthesis of Compound (A2-1)

(A2-1)

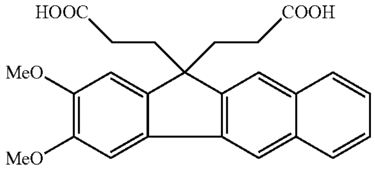

4.5 g of a compound (A2-1) (yield: 59%) was obtained in the same manner as in Synthesis Example 1, except that the compound (SA-1) was changed to the compound (SA-2). An area % of the compound (A2-1) determined from the HPLC measurement was 96.2%, and the raw material compound (SA-2) was 0.1% or less. In addition, the transmittance of the compound (A2-1) at 420 nm was 99.0%.

$^1$H-NMR data of compound (A2-1) (400 MHz, DMSO-$d_6$): δ 1.35 to 1.45 ppm (m, 4H), 2.35 to 2.45 ppm (m, 4H), 3.80 ppm (s, 3H), 3.90 ppm (s, 3H), 7.15 ppm (s, 1H), 7.35 to 7.50 ppm (m, 2H), 7.60 ppm (s, 1H), 7.85 to 7.90 ppm (m, 3H), 8.20 ppm (s, 1H), 11.9 ppm (s, 2H)

Synthesis Example 3: Synthesis of Compound (A3-1)

(A3-1)

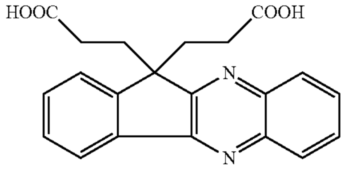

5.5 g of a compound (A3-1) (yield: 70%) was obtained in the same manner as in Synthesis Example 1, except that the compound (SA-1) was changed to the compound (SA-3). An area % of the compound (A3-1) determined from the HPLC measurement was 97.1%, and the raw material compound (SA-3) was 0.1% or less. In addition, the transmittance of the compound (A3-1) at 420 nm was 99.1%.

$^1$H-NMR data of compound (A3-1) (400 MHz, DMSO-$d_6$): δ 1.50 to 1.75 ppm (m, 4H), 2.35 to 2.55 ppm (m, 4H), 7.62 ppm (t, 1H), 7.70 ppm (t, 1H), 7.75 to 7.90 ppm (m, 3H), 8.15 to 8.25 ppm (m, 3H), 12.0 ppm (s, 2H)

Synthesis Example 4: Synthesis of Compound (A4-1)

(A4-1)

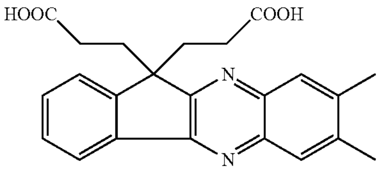

6.2 g of a compound (A4-1) (yield: 78%) was obtained in the same manner as in Synthesis Example 1, except that the compound (SA-1) was changed to the compound (SA-4). An area % of the compound (A4-1) determined from the HPLC measurement was 97.6%, and the raw material compound (SA-4) was 0.1% or less. In addition, the transmittance of the compound (A4-1) at 420 nm was 98.9%.

$^1$H-NMR data of compound (A4-1) (400 MHz, DMSO-$d_6$): δ 1.50 to 1.75 ppm (m, 4H), 2.35 to 2.55 ppm (m, 10H), 7.55 ppm (t, 1H), 7.62 ppm (t, 1H), 7.76 ppm (d, 1H), 7.90 to 7.95 ppm (m, 2H), 8.10 ppm (d, 1H), 12.0 ppm (s, 2H)

Synthesis Example 5: Synthesis of Compound (A5-1)

(A5-1)

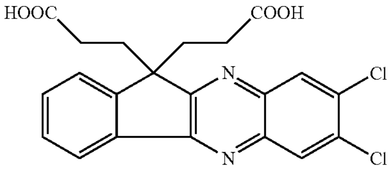

6.7 g of a compound (A5-1) (yield: 89%) was obtained in the same manner as in Synthesis Example 1, except that the compound (SA-1) was changed to the compound (SA-5). An area % of the compound (A5-1) determined from the HPLC measurement was 95.9%, and the raw material compound (SA-5) was 0.1% or less. In addition, the transmittance of the compound (A5-1) at 420 nm was 98.7%.

$^1$H-NMR data of compound (A5-1) (400 MHz, DMSO-$d_6$): δ 1.55 to 1.80 ppm (m, 4H), 2.35 to 2.55 ppm (m, 4H), 7.60 ppm (t, 1H), 7.75 ppm (t, 1H), 7.80 ppm (d, 1H), 8.12 ppm (d, 1H), 8.40 to 8.50 ppm (m, 2H), 12.0 ppm (s, 2H)

Synthesis Example 6: Synthesis of Compound (A1-1)

5.2 g of the compound (A1-1) (yield: 62%) was obtained in the same manner as in Synthesis Example 1, except that the solvent used in the reaction was changed N,N-dimethylacetamide (SP value: 24.8 $MPa^{1/2}$) to acetonitrile (SP value: 24.6 $MPa^{1/2}$). An area % of the compound (A1-1) determined from the HPLC measurement was 96.1%, and the raw material compound (SA-1) was 0.1% or less. In addition, the transmittance of the compound (A1-1) at 420 nm was 99.0%.

Reference Example 1: Synthesis of Compound (A1-1)

4.1 g of the compound (A1-1) (yield: 49%) was obtained in the same manner as in Synthesis Example 1, except that the solvent used in the reaction was changed N,N-dimethylacetamide (SP value: 24.8 $MPa^{1/2}$) to 1,4-dioxane (SP value: 20.5 $MPa^{1/2}$). An area % of the compound (A1-1) determined from the HPLC measurement was 89.7%, and 5.5% of the raw material compound (SA-1) remained. In addition, the transmittance of the compound (A1-1) at 420 nm was 97.9%.

Even in a case where the temperature at which the addition reaction was carried out was increased, the residual ratio of the raw material compound hardly changed.

As described above, the compound according to the embodiment of the present invention had a high transmittance of 97.9% or more at 420 nm, and coloration was less likely to occur.

In addition, as compared with the example of synthesizing the compound (A1-1) from the compound (SA-1), by using the solvent having an SP value of 21.0 $MPa^{1/2}$ or more in the addition reaction, a compound having a transmittance of 99.0% or more and having more suppressed coloration could be obtained (Synthesis Examples 1 and 6 with respect to Reference Example 1).

Reference Example 2: Cured Product of Curable Monomer Using Compound According to Embodiment of Present Invention as Synthetic Intermediate

[Synthesis of compounds (MA1-1) to (MA5-1)]

The following compounds (MA1-1) to (MA5-1) were synthesized as follows using the compounds (A1-1) to (A5-1) synthesized in Synthesis Examples 1 to 5 above.

Reference Example 2-1: Synthesis of Compound (MA1-1)

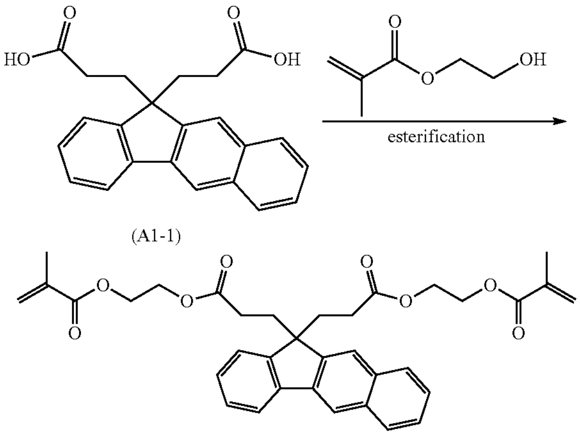

(A1-1)

(MA1-1)

4.0 g of the compound (A1-1), 20 mL of dichloromethane, 3.3 g of 2-hydroxyethyl methacrylate, 0.1 g of N,N-dimethylaminopyridine, and 4.9 g of 1-ethyl-3-(3-dimethylaminopropyl)carbodiimide hydrochloride were mixed with each other. After stirring at 40° C. for 2 hours, 1N hydrochloric acid was added thereto, the mixture was washed and liquid-separated, a 5% sodium hydrogen carbonate aqueous solution was added thereto, and the mixture was washed and liquid-separated. After dehydration with magnesium sulfate, filtration, and concentration, purification was performed by column chromatography (eluent: mixed solution of chloroform and methanol) to obtain 5.4 g of the compound (MA1-1) (yield: 83%).

$^1$H-NMR of compound (MA1-1) (400 MHz, $CDCl_3$): δ=1.65 to 1.85 ppm (m, 4H), 1.89 ppm (s, 6H), 2.45 to 2.55 ppm (m, 4H), 4.15 to 4.25 ppm (m, 8H), 5.55 ppm (s, 2H), 6.05 ppm (s, 2H), 7.35 to 7.55 ppm (m, 6H), 7.78 ppm (s, 1H), 7.82 to 7.95 ppm (m, 2H), 8.15 ppm (s, 1H)

Absorption spectrum (absorbance) of the compound (MA1-1) was measured by the following procedure.

The compound was precisely weighed in an amount of 50 mg, diluted with tetrahydrofuran (THF) using a 5 mL volumetric flask, and further diluted with THF so that the solution concentration was 1/500 times to prepare a measurement solution. The measurement was performed using UV-2550 (product name) manufactured by Shimadzu Corporation.

First, a square quartz cell (cell length: 10 mm) containing a control sample (THF) in both the sample optical path and the control optical path was placed, and the absorbance in a wavelength region of 250 to 800 nm was adjusted to zero. Next, the sample in the sample optical path-side cell was replaced with the measurement solution of the compound prepared above, and the absorption spectrum at 250 to 800 nm was measured.

A wavelength λmax of the maximal peak on the longest wavelength side in a range of 300 to 400 nm, which was obtained from the measurement result, was 343 nm.

Reference Example 2-2: Synthesis of Compound (MA2-1)

(MA2-1)

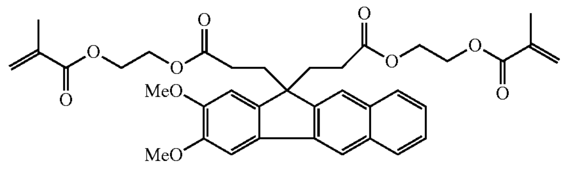

4.9 g of the compound (MA2-1) (yield: 80%) was obtained in the same manner as in Reference Example 2-1, except that the compound (A1-1) was changed to the compound (A2-1).

$^1$H-NMR of compound (MA2-1) (400 MHz, $CDCl_3$): δ=1.65 to 1.85 ppm (m, 4H), 1.89 ppm (s, 6H), 2.45 to 2.55 ppm (m, 4H), 3.96 ppm (s, 3H), 4.02 ppm (s, 3H), 4.15 to 4.25 ppm (m, 8H), 5.55 ppm (s, 2H), 6.05 ppm (s, 2H), 6.85 ppm (s, 1H), 7.35 ppm (s, 1H), 7.40 to 7.55 ppm (m, 2H), 7.71 ppm (s, 1H), 7.80 to 7.93 ppm (m, 2H), 8.00 ppm (s, 1H)

A wavelength λmax of the maximum peak of the compound (MA2-1) on the longest wavelength side in a range of 300 to 400 nm, which was measured in the same manner as that of the compound (MA1-1), was 354 nm.

Reference Example 2-3: Synthesis of Compound (MA3-1)

(MA3-1)

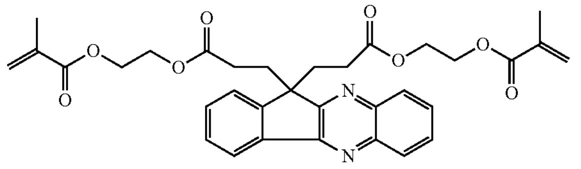

5.2 g of the compound (MA3-1) (yield: 80%) was obtained in the same manner as in Reference Example 2-1, except that the compound (A1-1) was changed to the compound (A3-1).

$^1$H-NMR data of compound (MA3-1) (400 MHz, $CDCl_3$): δ=1.65 to 1.85 ppm (m, 4H), 1.89 ppm (s, 6H), 2.38 to 2.48 ppm (m, 2H), 2.68 to 2.78 ppm (m, 2H), 4.15 to 4.25 ppm (m, 8H), 5.55 ppm (s, 2H), 6.05 ppm (s, 2H), 7.55 to 7.65 ppm (m, 3H), 7.80 to 7.95 ppm (m, 2H), 8.10 to 8.25 ppm (m, 3H)

A wavelength λmax of the maximum peak of the compound (MA3-1) on the longest wavelength side in a range of 300 to 400 nm, which was measured in the same manner as that of the compound (MA1-1), was 360 nm.

Reference Example 2-4: Synthesis of Compound (MA4-1)

(MA4-1)

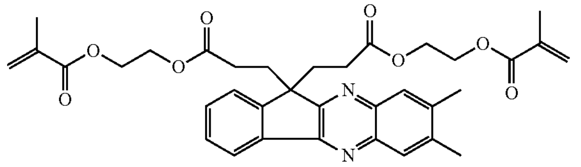

4.4 g of the compound (MA4-1) (yield: 70%) was obtained in the same manner as in Reference Example 2-1, except that the compound (A1-1) was changed to the compound (A4-1).

$^1$H-NMR of compound (MA4-1) (400 MHz, $CDCl_3$): δ=1.65 to 1.85 ppm (m, 4H), 1.89 ppm (s, 6H), 2.35 to 2.45 ppm (m, 2H), 2.50 ppm (s, 3H), 2.52 ppm (s, 3H), 2.65 to 2.75 ppm (m, 2H), 4.15 to 4.25 ppm (m, 8H), 5.55 ppm (s, 2H), 6.05 ppm (s, 2H), 7.55 to 7.65 ppm (m, 3H), 7.88 ppm (s, 1H), 7.92 ppm (s, 1H), 8.20 ppm (d, 2H)

A wavelength λmax of the maximum peak of the compound (MA4-1) on the longest wavelength side in a range of 300 to 400 nm, which was measured in the same manner as that of the compound (MA1-1), was 369 nm.

Reference Example 2-5: Synthesis of Compound (MA5-1)

(MA5-1)

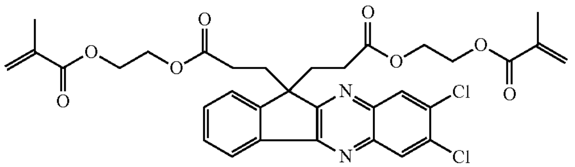

5.1 g of the compound (MA5-1) (yield: 84%) was obtained in the same manner as in Reference Example 2-1, except that the compound (A1-1) was changed to the compound (A5-1).

$^1$H-NMR of compound (MA5-1) (400 MHz, $CDCl_3$): δ=1.65 to 1.85 ppm (m, 4H), 1.89 ppm (s, 6H), 2.35 to 2.45 ppm (m, 2H), 2.65 to 2.75 ppm (m, 2H), 4.15 to 4.25 ppm (m, 8H), 5.55 ppm (s, 2H), 6.05 ppm (s, 2H), 7.55 to 7.65 ppm (m, 3H), 8.16 ppm (d, 1H), 8.24 ppm (s, 1H), 8.28 ppm (s, 1H)

A wavelength λmax of the maximum peak of the compound (MA5-1) on the longest wavelength side in a range of 300 to 400 nm, which was measured in the same manner as that of the compound (MA1-1), was 372 nm.

[Synthesis of Comparative Compound (CA-3)]

[Synthesis of Intermediate 4]

An intermediate 4 was synthesized according to the description in paragraph 0133 of WO2017/115649A.

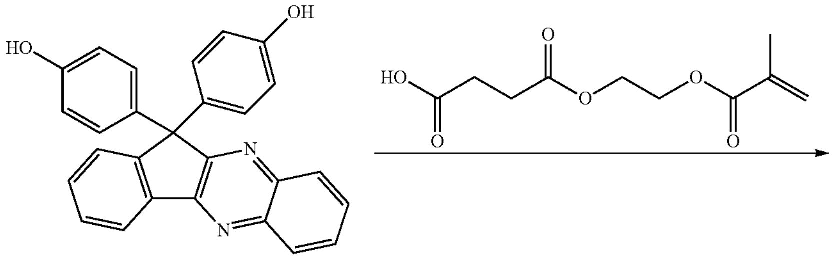

Intermediate 4

-continued

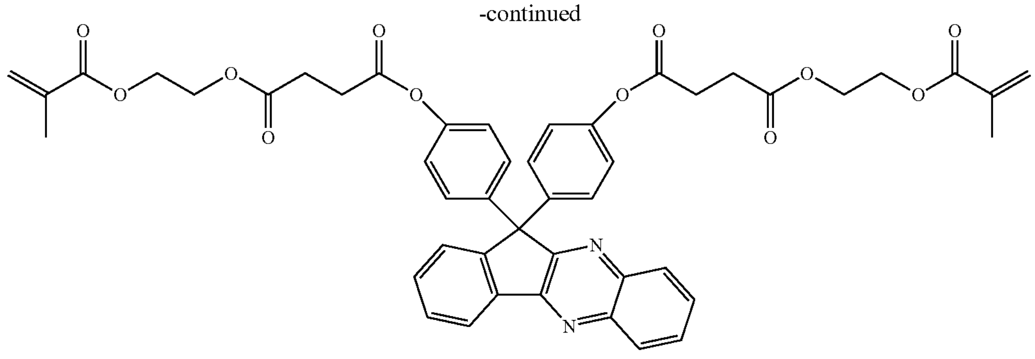

(CA-3)

Into a 200 mL three-neck flask, 4.8 g of the intermediate 4, 6.5 g of mono(2-methacryloyloxyethyl) succinate, 140 mg of N,N-dimethylaminopyridine (DMAP), and 50 mL of dichloromethane were charged, and the mixture was stirred in an ice bath for 10 minutes. 5.8 g of 1-(3-dimethylaminopropyl)-3-ethylcarbodiimide hydrochloride (EDAC·HCl) was added thereto, and the mixture was reacted at room temperature for 4 hours. The reaction solution was diluted with ethyl acetate, and washed with water, saturated sodium hydrogen carbonate aqueous solution, and saturated saline in this order, and the organic layer was dried with magnesium sulfate. After removing the magnesium sulfate by filtration, the obtained product was purified by silica gel column chromatography using ethyl acetate/hexane as a developing solvent to obtain 7.5 g of a comparative compound (CA-3).

A wavelength λmax of the maximum peak of the comparative compound (CA-3) on the longest wavelength side in a range of 300 to 400 nm, which was measured in the same manner as that of the compound (MA1-1), was 367 nm.

[Synthesis of Comparative Compound (CA-4)]

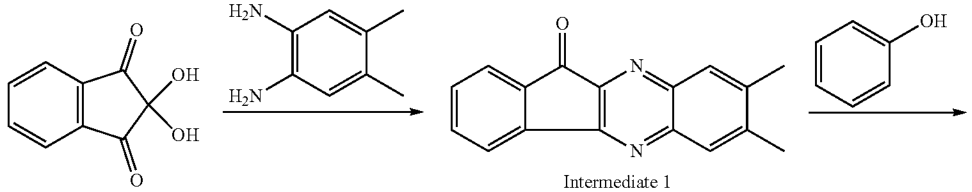

Intermediate 1

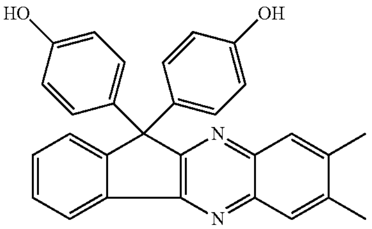

Intermediate 2

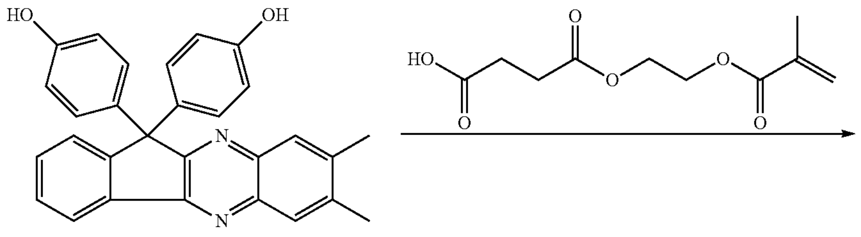

Intermediate 2

-continued

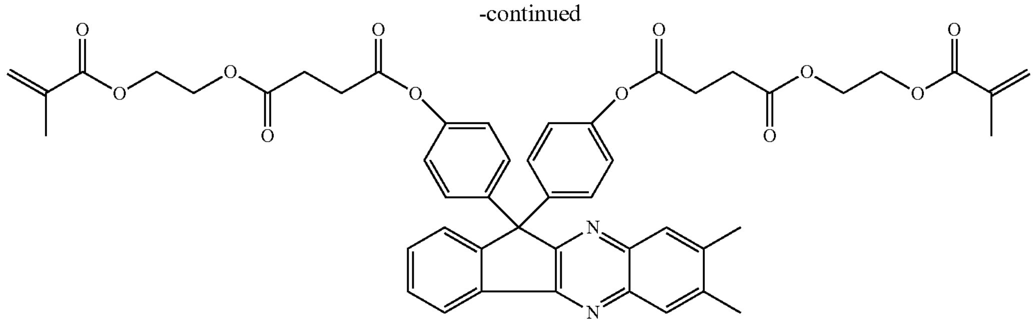

(CA-4)

[Synthesis of Intermediate 1]

50 mL of ethanol and 10 mL of acetic acid were added to 25.6 g of 4,5-dimethyl-1,2-phenylenediamine and 35.6 g of ninhydrin, and the mixture was reacted at 70° C. for 3 hours. The reaction solution was cooled to room temperature, and the precipitated crystals were collected by filtration, washed with ethanol, and dried to obtain 41.1 g of an intermediate 1.

[Synthesis of Intermediate 2]

22 g of the intermediate 1 and 32 g of phenol were dissolved in 20 mL of methanesulfonic acid and 20 mL of acetonitrile. The reaction solution was heated, and 0.3 mL of 3-mercaptopropionic acid was added dropwise thereto while maintaining the temperature at 90° C. After stirring for 3 hours, 200 mL of acetonitrile and 100 mL of water were added thereto, and the reaction solution was stirred in an ice bath for 2 hours. The precipitated crystals were collected by filtration, washed with methanol, and dried to obtain 26 g of an intermediate 2.

[Synthesis of Comparative Compound (CA-4)]

A comparative compound (CA-4) was obtained in the same manner as in the above-described synthesis of the comparative compound (CA-3), except that the intermediate 4 was changed to the intermediate 2.

A wavelength λmax of the maximum peak of the comparative compound (CA-4) on the longest wavelength side in a range of 300 to 400 nm, which was measured in the same manner as that of the compound (MA1-1), was 374 nm.

[Synthesis of Comparative Compound (CA-5)]

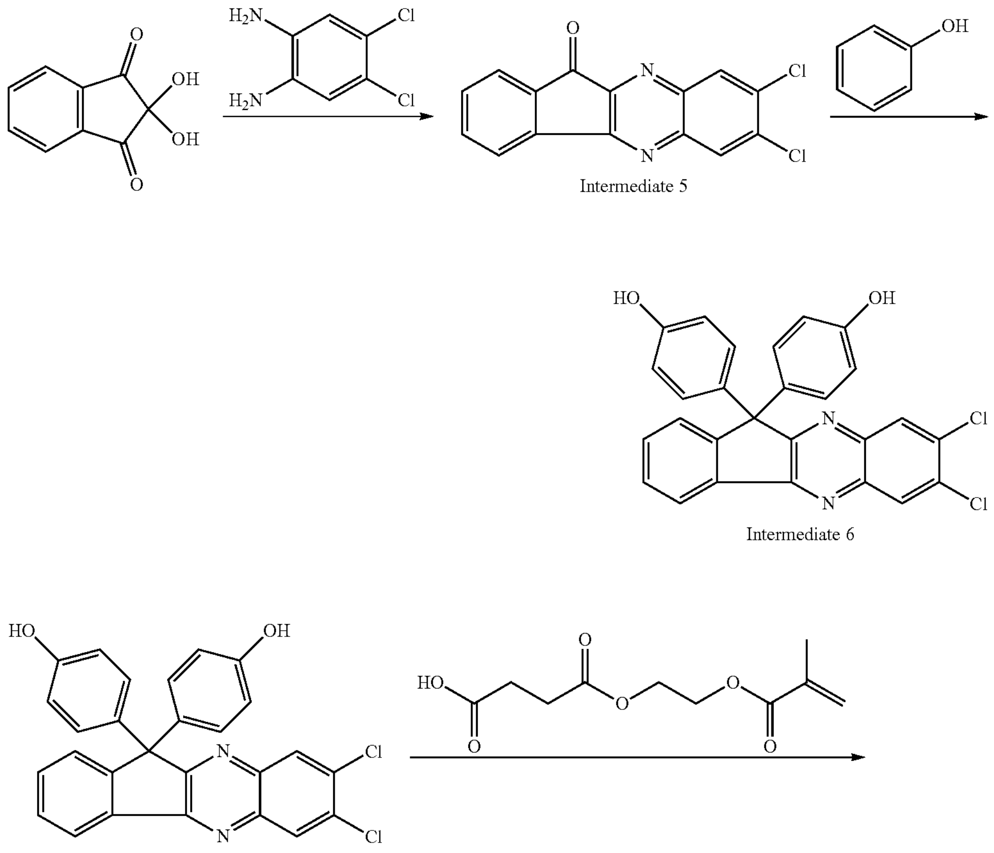

Intermediate 5

Intermediate 6

Intermediate 6

-continued

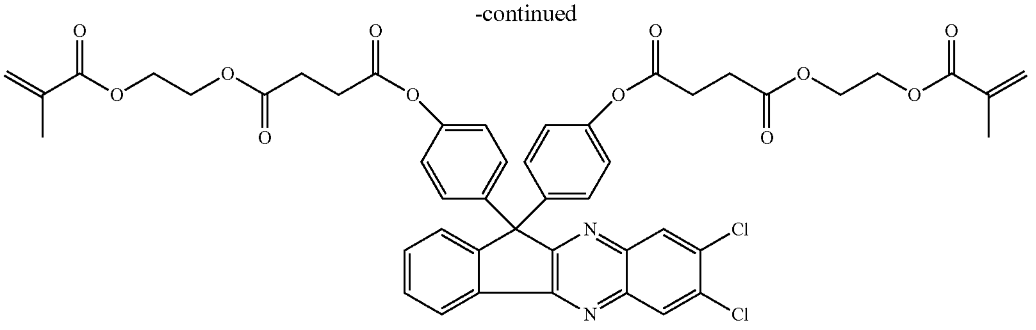

(CA-5)

[Synthesis of Intermediate 5]

An intermediate 5 was obtained in the same manner as in the above-described synthesis of the intermediate 1, except that 4,5-dimethyl-1,2-phenylenediamine was changed to 4,5-dichloro-1,2-phenylenediamine.

[Synthesis of Intermediate 6]

An intermediate 6 was obtained in the same manner as in the above-described synthesis of the intermediate 2, except that the intermediate 1 was changed to the intermediate 5.

[Synthesis of Comparative Compound (CA-5)]

A comparative compound (CA-5) was obtained in the same manner as in the above-described synthesis of the comparative compound (CA-3), except that the intermediate 4 was changed to the intermediate 6.

A wavelength λmax of the maximum peak of the comparative compound (CA-5) on the longest wavelength side in a range of 300 to 400 nm, which was measured in the same manner as that of the compound (MA1-1), was 377 nm.

[Synthesis of Polymer Having Radically Polymerizable Group in Side Chain]

A polymer (G-1) having a radically polymerizable group in the side chain was synthesized by the following method.

12.0 g of benzyl methacrylate and 18.0 g of allyl methacrylate were dissolved in 172.3 g of methyl ethyl ketone, and the mixture was heated to 70° C. The solution was added dropwise over 30 minutes to a solution in which 1.05 g of a polymerization initiator V-65 (product name, manufactured by FUJIFILM Wako Pure Chemical Corporation, oil-soluble azo polymerization initiator) was dissolved in 12.0 g of methyl ethyl ketone. After the completion of the dropwise addition, the reaction was further performed at 70° C. for 4.5 hours. The reaction solution was allowed to cool and concentrated until the total amount thereof reached 107.7 g, and then 42.0 g of methanol was added thereto and stirred until the reaction solution was homogeneous. The reaction solution was added dropwise to 858.0 g of methanol cooled to 5° C. or lower, and the precipitated powder was collected by filtration and dried. In this way, 20.5 g of the polymer (G-1) was obtained. The weight-average molecular weight of the obtained polymer was 35700, and the dispersibility (Mw/Mn) was 3.3.

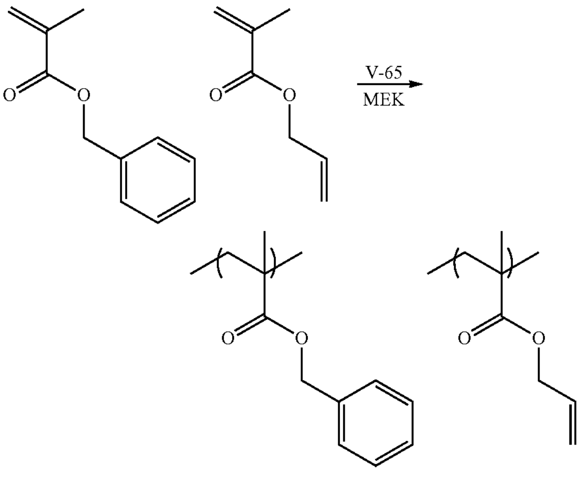

G-1

The weight-average molecular weight and the dispersibility of the polymer produced above are a weight-average molecular weight and a dispersibility in terms of standard polystyrene by gel permeation chromatography (GPC), and are values measured under the following conditions.

Measuring instrument: HLC-8320GPC (product name, manufactured by Tosoh Corporation)

Column: connection of TOSOH TSKgel HZM-H (product name, manufactured by Tosoh Corporation), TOSOH TSKgel HZ4000 (product name, manufactured by Tosoh Corporation), and TOSOH TSKgel HZ2000 (product name, manufactured by Tosoh Corporation)

Carrier: THF

Measurement temperature: 40° C.

Carrier flow rate: 0.35 ml/min

Sample concentration: 0.1% by mass

Detector: refractive index (RI) detector

Reference Example 3: Preparation of Curable Resin Composition

A curable monomer obtained from the compound represented by General Formula (A) or (B) or a comparative curable monomer (also referred to as a comparative compound), other monomers, a photopolymerization initiator, a thermal polymerization initiator, and other additives were mixed and stirred to be homogeneous, a curable resin composition was prepared so as to have a composition shown in Table 1 below.

[Evaluation 1] Measurement of Viscosity of Curable Resin Composition

A viscosity of the produced curable resin composition was measured using a reometer (product name: RS600) manufactured by HAAKE under the conditions of 25° C. and a shear rate of 10 $s^{-1}$. The results are summarized in Table 1.

Reference Example 4: Production of Cured Product

The obtained curable resin composition was injected into a circular transparent glass mold having a diameter of 20 mm so that a thickness of a cured product was 1 mm. The glass mold is made of borosilicate glass in which a surface is hydrophobically treated with dichlorodimethylsilane.

Using Execure 3000 (product name, manufactured by HOYA CORPORATION) as a light source, a photocured sample was produced by irradiating ultraviolet rays of 1000 $mJ/cm^2$ from above the transparent glass mold in a nitrogen-substituted atmosphere so that an oxygen concentration was 1% or less. Subsequently, the obtained photocured sample was heated at 200° C. for 30 minutes in an atmosphere having an oxygen concentration of 1% or less to produce a cured product in which the curing reaction completely proceeded.

[Evaluation 2] Evaluation of Refractive Index of Cured Product

A refractive index nD of the obtained cured product at a wavelength of 589 nm was measured under a condition of 25° C. using an Abbe refractionometer (manufactured by ATAGO CO., LTD., product name: DR-M4). In addition, nF, nC, and ng were also measured, and as wavelength dispersion characteristics of the refractive index, the Abbe number νD and the partial dispersion ratio θg, F were obtained from the following expressions. The results are summarized in Table 1.

$$\nu D=(nD-1)/(nF-nC)$$

$$\theta g,F=(ng-nF)/(nF-nC)$$

Here, nF represents a refractive index at a wavelength of 486 nm, nC represents a refractive index at a wavelength of 656 nm, and ng represents a refractive index at a wavelength of 436 nm.

[Evaluation 3] Evaluation of Transmittance of Cured Product

With regard to the obtained cured product, using an ultraviolet-visible spectrophotometer UV-2600 (product name, manufactured by Shimadzu Corporation), an ultraviolet-visible transmittance measurement was performed on a central portion (5 mm in diameter) to measure a transmittance at a wavelength of 420 nm. The results are summarized in Table 1.

[Evaluation 4] Birefringence Index Δn

Using a birefringence evaluation device (WPA-100 (product name), manufactured by Photonic Lattice, Inc.), a birefringence within a circle having a diameter of 10 mm including the center of the cured product (cured product sample for optical measurement) produced above at a wavelength of 543 nm was measured, and the average value thereof was defined as a birefringence index Δn.

All of cured products obtained from the curable resin compositions No. 101 to 115 had a small birefringence Δn of 0.0003 to 0.0009, and could obtain a clear image without shifting an imaging position, so that the cured product was suitable for use as an optical member of an imaging module

TABLE 1-1

| | | Curable resin composition | 101 | 102 | 103 | 104 |
|---|---|---|---|---|---|---|
| Composition | Curable monomer obtained from compound represented by General Formula (A) or (B) | MA1-1 | 80 | 85 | — | — |
| | | MA2-1 | — | — | 80 | 85 |
| | | MA3-1 | — | — | — | — |
| | | MA4-1 | — | — | — | — |
| | | MA5-1 | — | — | — | — |
| | Other monomers | PEA | 19.8 | 14.8 | 19.8 | 14.8 |
| | | OPPE | — | — | — | — |
| | | BzMA | — | — | — | — |
| | | HDDMA | — | — | — | — |
| | Photopolymerization initiator | Irg819 | — | — | — | — |
| | | IrgTPO | 0.1 | 0.1 | 0.1 | 0.1 |
| | Thermal polymerization initiator | PERHEXYL D | 0.1 | 0.1 | 0.1 | 0.1 |
| | Other additives | G-1 | — | — | — | — |
| | Total | | 100 | 100 | 100 | 100 |
| Evaluation | Viscosity of curable resin composition (cP) | | 5400 | 14500 | 6200 | 17900 |
| | Refractive index characteristics of cured product | nD | 1.619 | 1.622 | 1.609 | 1.611 |
| | | νD | 21.2 | 20.8 | 20.1 | 19.5 |
| | | θg, F | 0.67 | 0.67 | 0.72 | 0.72 |
| | Transmittance of cured product | | 85.0% | 84.1% | 82.7% | 81.4% |

| | | Curable resin composition | 105 | 106 | 107 | 108 |
|---|---|---|---|---|---|---|
| Composition | Curable monomer obtained from compound represented by General Formula (A) or (B) | MA1-1 | — | — | — | — |
| | | MA2-1 | — | — | — | — |
| | | MA3-1 | 45 | 55 | 65 | 75 |
| | | MA4-1 | — | — | — | — |
| | | MA5-1 | — | — | — | — |
| | Other monomers | PEA | 19.8 | 19.8 | 19.8 | 19.8 |
| | | OPPE | 25 | 15 | 10 | — |
| | | BzMA | — | — | — | — |
| | | HDDMA | — | — | — | 5 |

TABLE 1-1-continued

| | | | | | | |
|---|---|---|---|---|---|---|
| | Photopolymerization initiator | Irg819 | 0.1 | 0.1 | 0.1 | 0.1 |
| | | IrgTPO | — | — | — | — |
| | Thermal polymerization initiator | PERHEXYL D | 0.1 | 0.1 | 0.1 | 0.1 |
| | Other additives | G-1 | 10 | 10 | 5 | — |
| | Total | | 100 | 100 | 100 | 100 |
| Evaluation | Viscosity of curable resin composition (cP) | | 1800 | 2400 | 2200 | 1900 |
| | Refractive index characteristics of cured product | nD | 1.586 | 1.591 | 1.596 | 1.599 |
| | | νD | 22.8 | 22.0 | 21.3 | 20.6 |
| | | θg, F | 0.73 | 0.76 | 0.78 | 0.79 |
| | Transmittance of cured product | | 76.8% | 75.9% | 74.3% | 72.6% |

| | | Curable resin composition | 109 | 110 |
|---|---|---|---|---|
| Composition | Curable monomer obtained from compound represented by General Formula (A) or (B) | MA1-1 | — | — |
| | | MA2-1 | — | — |
| | | MA3-1 | 80 | 85 |
| | | MA4-1 | — | — |
| | | MA5-1 | — | — |
| | Other monomers | PEA | 19.8 | 14.8 |
| | | OPPE | — | — |
| | | BzMA | — | — |
| | | HDDMA | — | — |
| | Photopolymerization initiator | Irg819 | 0.1 | 0.1 |
| | | IrgTPO | — | — |
| | Thermal polymerization initiator | PERHEXYL D | 0.1 | 0.1 |
| | Other additives | G-1 | — | — |
| | Total | | 100 | 100 |
| Evaluation | Viscosity of curable resin composition (cP) | | 4100 | 9600 |
| | Refractive index characteristics of cured product | nD | 1.601 | 1.604 |
| | | νD | 20.1 | 19.6 |
| | | θg, F | 0.81 | 0.83 |
| | Transmittance of cured product | | 71.7% | 70.5% |

| | | Curable resin composition | 111 | 112 | 113 | 114 | 115 |
|---|---|---|---|---|---|---|---|
| Composition | Curable monomer obtained from compound represented by General Formula (A) or (B) | MA1-1 | — | — | — | — | — |
| | | MA2-1 | — | — | — | — | — |
| | | MA3-1 | — | — | — | — | — |
| | | MA4-1 | 80 | 85 | — | — | — |
| | | MA5-1 | — | — | 80 | 85 | 85 |
| | Other monomers | PEA | 19.8 | 14.8 | 19.8 | 14.8 | — |
| | | OPPE | — | — | — | — | — |
| | | BzMA | — | — | — | — | 14.8 |
| | | HDDMA | — | — | — | — | — |
| | Photopolymerization initiator | Irg819 | 0.1 | 0.1 | 0.1 | 0.1 | 0.1 |
| | | IrgTPO | — | — | — | — | — |
| | Thermal polymerization initiator | PERHEXYL D | 0.1 | 0.1 | 0.1 | 0.1 | 0.1 |
| | Other additives | G-1 | — | — | — | — | — |
| | Total | | 100 | 100 | 100 | 100 | 100 |
| Evaluation | Viscosity of curable resin composition (cP) | | 3200 | 7200 | 4600 | 12000 | 11600 |
| | Refractive index characteristics of cured product | nD | 1.600 | 1.603 | 1.610 | 1.613 | 1.614 |
| | | νD | 18.5 | 18.0 | 17.9 | 17.4 | 17.4 |
| | | θg, F | 0.85 | 0.87 | 0.89 | 0.92 | 0.91 |
| | Transmittance of cured product | | 73.1% | 72.8% | 67.3% | 66.1% | 66.6% |

| | | Curable resin composition | c11 | c12 | c13 |
|---|---|---|---|---|---|
| Composition | Comparative curable monomer | CA-1 | 80 | — | — |
| | | CA-2 | — | 80 | — |
| | | CA-3 | — | — | 80 |
| | | CA-4 | — | — | — |
| | | CA-5 | — | — | — |
| | | CA-6 | — | — | — |
| | Other monomers | PEA | 19.8 | 19.8 | 19.8 |
| | | OPPE | — | — | — |
| | | BzMA | — | — | — |
| | | HDDMA | — | — | — |

TABLE 1-1-continued

| | | | | | |
|---|---|---|---|---|---|
| | Photopolymerization initiator | Irg819 | — | — | 0.1 |
| | | IrgTPO | 0.1 | 0.1 | — |
| | Thermal polymerization initiator | PERHEXYL D | 0.1 | 0.1 | 0.1 |
| | Other additives | G-1 | — | — | — |
| | Total | | 100 | 100 | 100 |
| Evaluation | Viscosity of curable resin composition (cP) | | 86000 | 195000 | 77000 |
| | Refractive index characteristics of cured product | nD | 1.638 | 1.629 | 1.606 |
| | | νD | 21.8 | 20.4 | 21.1 |
| | | θg, F | 0.67 | 0.72 | 0.79 |
| | Transmittance of cured product | | 79.6% | 76.7% | 65.1% |

| | | Curable resin composition | c14 | c15 | c16 |
|---|---|---|---|---|---|
| Composition | Comparative curable monomer | CA-1 | — | — | — |
| | | CA-2 | — | — | — |
| | | CA-3 | — | — | — |
| | | CA-4 | 80 | — | — |
| | | CA-5 | — | 80 | — |
| | | CA-6 | — | — | 80 |
| | Other monomers | PEA | 19.8 | 19.8 | 19.8 |
| | | OPPE | — | — | — |
| | | BzMA | — | — | — |
| | | HDDMA | — | — | — |
| | Photopolymerization initiator | Irg819 | 0.1 | 0.1 | 0.1 |
| | | IrgTPO | — | — | — |
| | Thermal polymerization initiator | PERHEXYL D | 0.1 | 0.1 | 0.1 |
| | Other additives | G-1 | — | — | — |
| | Total | | 100 | 100 | 100 |
| Evaluation | Viscosity of curable resin composition (cP) | | 59000 | 86000 | 135000 |
| | Refractive index characteristics of cured product | nD | 1.599 | 1.600 | 1.630 |
| | | νD | 20.4 | 20.2 | 20.9 |
| | | θg, F | 0.81 | 0.83 | 0.80 |
| | Transmittance of cured product | | 62.0% | 59.1% | 59.0% |

<Note to Table>

Each component in the tables is as follows. The blending amount ratio of each component described in the column of each component is based on mass, and "-" indicates that the component is not contained.

(Curable Monomer Obtained from Compound Represented by General Formula (A) or (B))

(MA1-1)

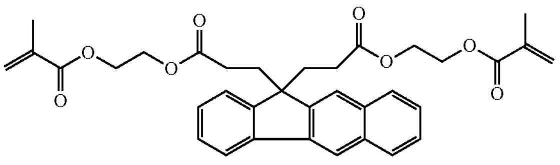

(MA2-1)

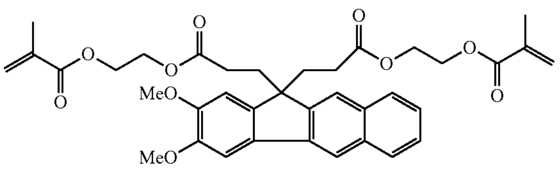

-continued (MA3-1)

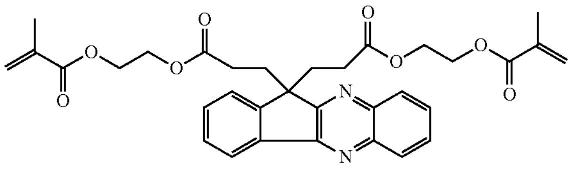

(MA4-1)

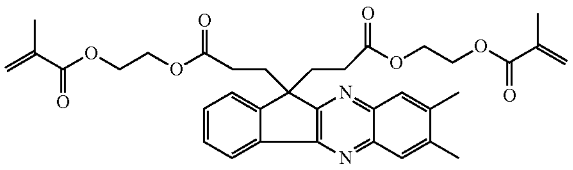

(MA5-1)

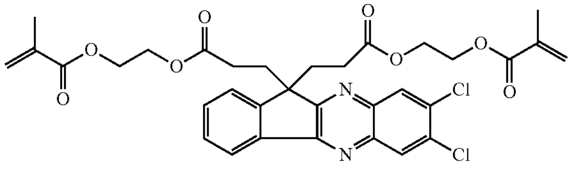

(Comparative Curable Monomer)
(CA-1)
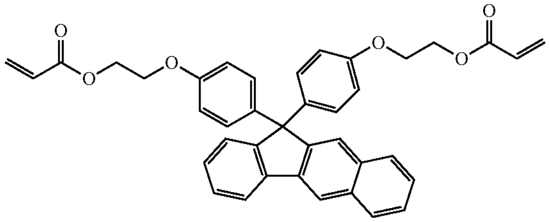
(CA-2)
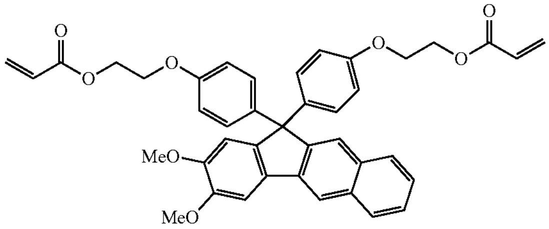
(CA-3)
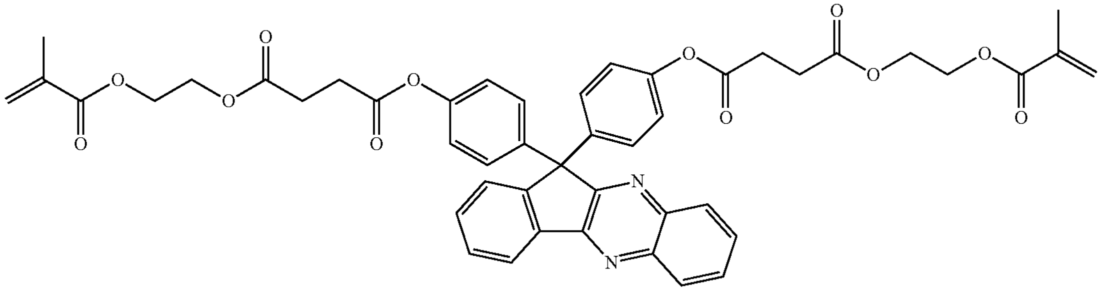
(CA-4)
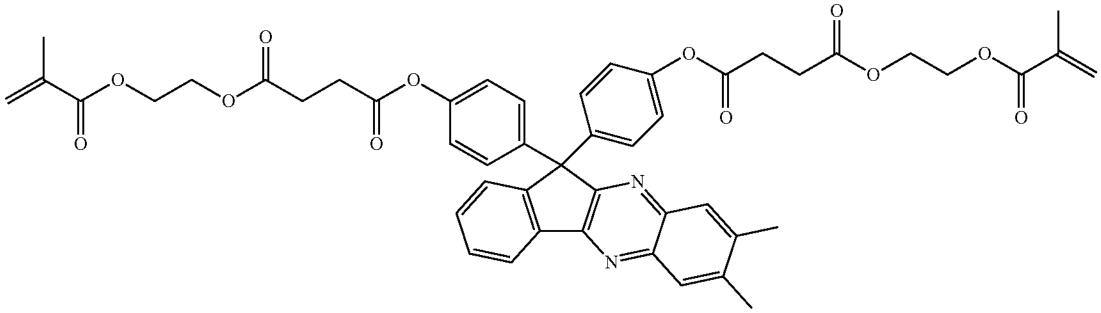
(CA-5)
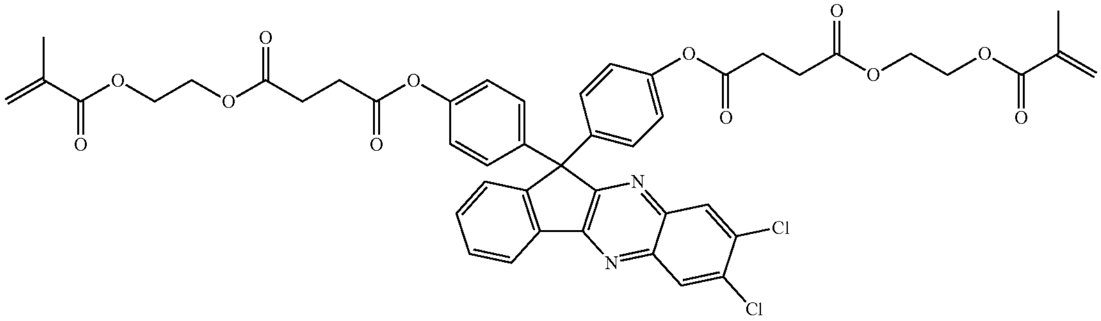
(CA-6)
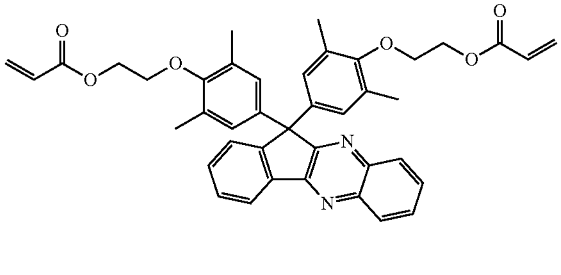

The comparative compound (CA-1) was synthesized according to the synthesis method described in Example 1 of JP2014-80572A.

The comparative compound (CA-2) was synthesized according to <Synthesis of compound 2-1> of WO2016/140245A.

The comparative compound (CA-6) was synthesized according to the synthesis of the compound (51) of WO2017/115649A (JP6606195B).

In a case where, similarly to the compound (MA1-1), the wavelengths λmax of the maximal peaks of the comparative compound (CA-1), the comparative compound (CA-2), and the comparative compound (CA-6) on the longest wavelength side in a range of 300 to 400 nm were measured, the comparative compound (CA-1) was 347 nm, the comparative compound (CA-2) was 359 nm, and the comparative compound (CA-6) was 368 nm.

(Other Monomers)

The compounds represented below are shown respectively.

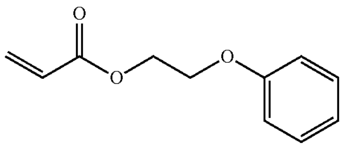

PEA

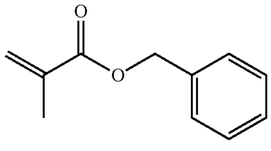

BzMA

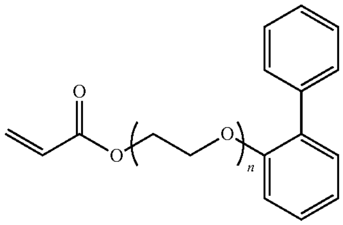

OPPE

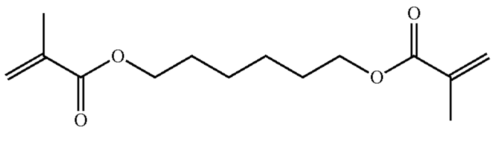

HDDMA n = 1-2

(Photopolymerization Initiator)

Irg819: Irgacure 819 (product name, manufactured by BASF SE)

IrgTPO: Irgacure TPO (product name, manufactured by BASF SE)

(Thermal polymerization initiator)

PERHEXYL D: product name, manufactured by NOF CORPORATION, di-tert-hexyl peroxide (Other Additives)

G-1: polymer (G-1) produced above

G-1

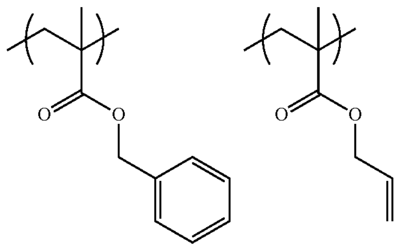

As shown in Table 1, it was found that, by using a curable monomer obtained from the compound according to the embodiment of the present invention, a cured product which achieved both a low Abbe number and a high transmittance at a high level, as compared with curable monomers in the related art, in which a phenylene group or a dimethylphenylene group was bonded to a fused-ring structure, was obtained.

In addition, in addition to the low Abbe number νD and the high transmittance described above, the cured product formed of the curable monomer obtained from the compound according to the embodiment of the present invention had a sufficiently high partial dispersion ratio θg, F of 0.67 or more, and was excellent in refractive index wavelength dispersion characteristics in a case of being used as a chromatic aberration correction lens.

The present invention has been described with the embodiments thereof, any details of the description of the present invention are not limited unless described otherwise, and it is obvious that the present invention is widely construed without departing from the gist and scope of the present invention described in the accompanying claims.

The present application claims the priority of JP2020-140313 filed in Japan on Aug. 21, 2020, the contents of which are incorporated herein by reference, as a part of the description of the present specification.

What is claimed is:

1. A compound represented by General Formula (A1-1),

General Formula (A1-1)

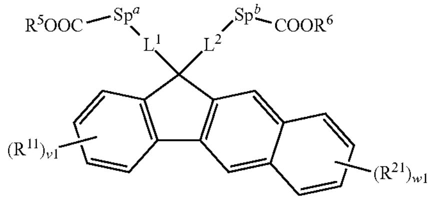

in the formulae, $R^5$ and $R^6$ each independently represent a hydrogen atom or an alkyl group, $L^1$ and $L^2$ each independently represent an alkylene group having 1 to 6 carbon atoms, and $Sp^a$ and $Sp^b$ each independently represent a single bond or a divalent linking group, $R^{11}$ and $R^{21}$ each independently represent a substituent, and v1 and w1 are each independently an integer of 0 to 4, provided that a structure represented by $(R^{11})_{v1}$-benzen ring/cyclopentadiene skeleton/naphthalene ring-$(R^{21})_{w1}$ is not line-symmetrical, where "/" represents that two rings described on left and right sides of the structure are fused.

2. A method for producing a compound represented by General Formula (A1-1), the method comprising:

obtaining a compound represented by General Formula (A1-1) by subjecting (i) an ethylenically unsaturated carboxylic acid compound, (ii) an ethylenically unsaturated carboxylic acid ester compound, (iii) an ethylenically unsaturated dicarboxylic acid anhydride, or (iv) an alkylcarboxylic acid ester compound having a leaving group at a ω-position to an addition reaction with a compound represented by General Formula (SA1-1) in the presence of a base, General Formua (SA1-1)

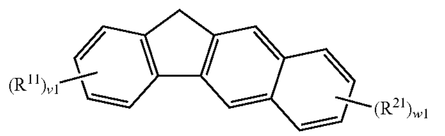

General Formula (A1-1)

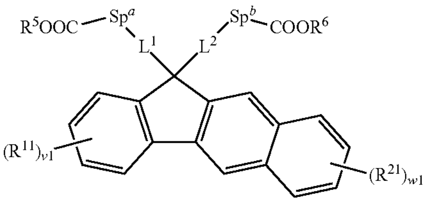

in the formulae, $R^5$ and $R^6$ each independently represent a hydrogen atom or an alkyl group, $L^1$ and $L^2$ each independently represent an alkylene group having 1 to 6 carbon atoms, and $Sp^a$ and $Sp^b$ each independently represent a single bond or a divalent linking group, $R^{11}$ and $R^{21}$ each independently represent a substituent, and v1 and w1 are each independently an integer of 0 to 4, provided that in General Formulae (SA1-1) and (A1-1), a structure represented by $(R^{11})_{v1}$-benzen ring/cyclopentadiene skeleton/naphthalene ring-$(R^{21})_{w1}$ is not line-symmetrical, where "/" represents that the two rings described on left and right sides of the structure are fused.

3. The method for producing a compound represented by General Formula (A1-1) according to claim 2, wherein, in (ii) to (iv), a hydrolysis reaction is carried out after the addition reaction.

4. The method for producing a compound represented by General Formula (A1-1) according to claim 2, wherein a solvent used in the addition reaction includes a solvent having an SP value of 21.0 $MPa^{1/2}$ or more.

* * * * *